US012580068B2

(12) United States Patent
Haemel et al.

(10) Patent No.: US 12,580,068 B2
(45) Date of Patent: Mar. 17, 2026

(54) VIRTUALIZED COMPUTING PLATFORM FOR INFERENCING, ADVANCED PROCESSING, AND MACHINE LEARNING APPLICATIONS

(71) Applicant: NVIDIA Corporation, San Jose, CA (US)

(72) Inventors: Nicholas Haemel, San Francisco, CA (US); Bojan Vukojevic, Pleasanton, CA (US); Risto Haukioja, Palo Alto, CA (US); Andrew Feng, Cupertino, CA (US); Yan Cheng, Great Falls, VA (US); Sachidanand Alle, Cambridge (GB); Daguang Xu, Potomac, MD (US); Holger Reinhard Roth, Rockville, MD (US); Johnny Israeli, San Jose, CA (US)

(73) Assignee: NVIDIA Corporation, Santa Clara, CA (US)

( * ) Notice: Subject to any disclaimer, the term of this patent is extended or adjusted under 35 U.S.C. 154(b) by 116 days.

(21) Appl. No.: 16/515,890

(22) Filed: Jul. 18, 2019

(65) Prior Publication Data

US 2020/0027210 A1     Jan. 23, 2020

Related U.S. Application Data

(60) Provisional application No. 62/700,071, filed on Jul. 18, 2018, provisional application No. 62/820,188, filed on Mar. 18, 2019.

(51) Int. Cl.
G06K 9/00      (2022.01)
G06F 9/455     (2018.01)
(Continued)

(52) U.S. Cl.
CPC ......... *G16H 30/20* (2018.01); *G06F 9/45558* (2013.01); *G06F 9/547* (2013.01);
(Continued)

(58) Field of Classification Search
CPC ....... G06K 9/00; H04L 67/2823; H04L 67/00; G06T 7/00
(Continued)

(56) References Cited

U.S. PATENT DOCUMENTS 10,853,148 B1 * 12/2020 Kenney ................ G06F 9/4881
2009/0080408 A1    3/2009 Natoli et al.
(Continued)

FOREIGN PATENT DOCUMENTS

CN        104008262 A      8/2014
CN        107492090 A      12/2017

OTHER PUBLICATIONS

International Search Report and Written Opinion in International Application No. PCT/US2019/042446 mailed Jan. 2, 2020. 23 Pages.
(Continued)

*Primary Examiner* — Seyed H Azarian
(74) *Attorney, Agent, or Firm* — Davis Wright Tremaine LLP

(57) ABSTRACT

In various examples, a virtualized computing platform for advanced computing operations—including image reconstruction, segmentation, processing, analysis, visualization, and deep learning—may be provided. The platform may allow for inference pipeline customization by selecting, organizing, and adapting constructs of task containers for local, on-premises implementation. Within the task containers, machine learning models generated off-premises may be leveraged and updated for location specific implementation to perform image processing operations. As a result, and
(Continued)

using the virtualized computing platform, facilities such as hospitals and clinics may more seamlessly train, deploy, and integrate machine learning models within a production environment for providing informative and actionable medical information to practitioners.

24 Claims, 11 Drawing Sheets

(51) Int. Cl.

| | |
|---|---|
| *G06F 9/54* | (2006.01) |
| *G06N 3/045* | (2023.01) |
| *G06N 5/043* | (2023.01) |
| *G06T 7/00* | (2017.01) |
| *G06T 7/10* | (2017.01) |
| *G06T 19/00* | (2011.01) |
| *G16H 30/20* | (2018.01) |

(52) U.S. Cl.
CPC ............. *G06N 3/045* (2023.01); *G06N 5/043* (2013.01); *G06T 7/0012* (2013.01); *G06T 7/10* (2017.01); *G06T 19/006* (2013.01); *G06F 2009/4557* (2013.01); *G06F 2009/45595* (2013.01)

(58) Field of Classification Search
USPC ....... 382/100, 128–133, 156, 168, 173, 181, 382/206, 214, 224, 254, 276, 285–291, 382/305; 709/203
See application file for complete search history.

(56) References Cited

U.S. PATENT DOCUMENTS

| | | | | |
|---|---|---|---|---|
| 2010/0063992 | A1* | 3/2010 | Ma ................... | H04N 21/64322 |
| | | | | 709/203 |
| 2013/0026783 | A1 | 1/2013 | Kakiuchi et al. | |
| 2016/0232658 | A1 | 8/2016 | Syeda-Mahmood | |
| 2017/0083380 | A1 | 3/2017 | Bishop et al. | |
| 2017/0213156 | A1* | 7/2017 | Hammond ............. | G06N 3/091 |
| 2018/0060512 | A1* | 3/2018 | Sorenson ......... | G06Q 10/06398 |
| 2018/0241834 | A1* | 8/2018 | Natoli ..................... | H04L 67/56 |
| 2018/0307945 | A1* | 10/2018 | Haigh ................... | G06N 3/096 |
| 2019/0163539 | A1* | 5/2019 | Bishop ................. | G06F 9/5083 |
| 2020/0366581 | A1* | 11/2020 | Layman ................ | G06Q 10/06 |

OTHER PUBLICATIONS

Koty, Ramchandra and Kannan, Balasubramaniyan. "The Rise of Container-as-a-service (CaaS) for Faster Application Delivery." Jan. 6, 2017. https://blog.equinix.com/blog/2017/01/06/the-rise-of-container-as-a-service-caas-for-faster-application-delivery/ (last visited Jan. 28, 2020). 3 Pages.

Wang, Chenxi. "Containers 101: Docker Fundamentals" Jun. 2, 2016. https://www.infoworld.com/article/3077875/containers-101-docker-fundamentals.html (last visited Jan. 28, 2020). 11 Pages.

Office Action for Chinese Application No. 201980062130.9, mailed Jun. 29, 2023, 22 pages.

Extended European Search Report for Application No. 21214343.2, mailed Mar. 16, 2022, 8 pages.

Office Action for Chinese Application No. 201980062130.9, mailed Mar. 8, 2024, 14 pages.

Office Action for European Application No. 197490956.6, mailed Mar. 22, 2024, 5 pages.

Powell et al., "Project Clara: NVIDIA Supercomputing Platform Redefines Medical Imaging," Retrieved from, https://web.archive.org/web/20190629122426/https://blogs.nvidia.com/blog/2018/03/28/ai-healthcare-gtc/, Mar. 28, 2018, 5 Pages.

Office Action for Chinese Application No. 201980062130.9, mailed Jun. 5, 2024, 18 pages.

Office Action for European Application No. 21214343.2, mailed Feb. 12, 2025, 7 pages.

\* cited by examiner

100

102

DEPLOYMENT
SYSTEM 106

118

SOFTWARE

120

SERVICES

122

HARDWARE

MODEL
REGISTRY
124

TRAINING SYSTEM 104

OUTPUT
MODEL
116

MODEL
TRAINING
114

LABELED
CLINIC
DATA
112

AI-ASSISTED
ANNOTATION
110

IMAGING
DATA
108

500

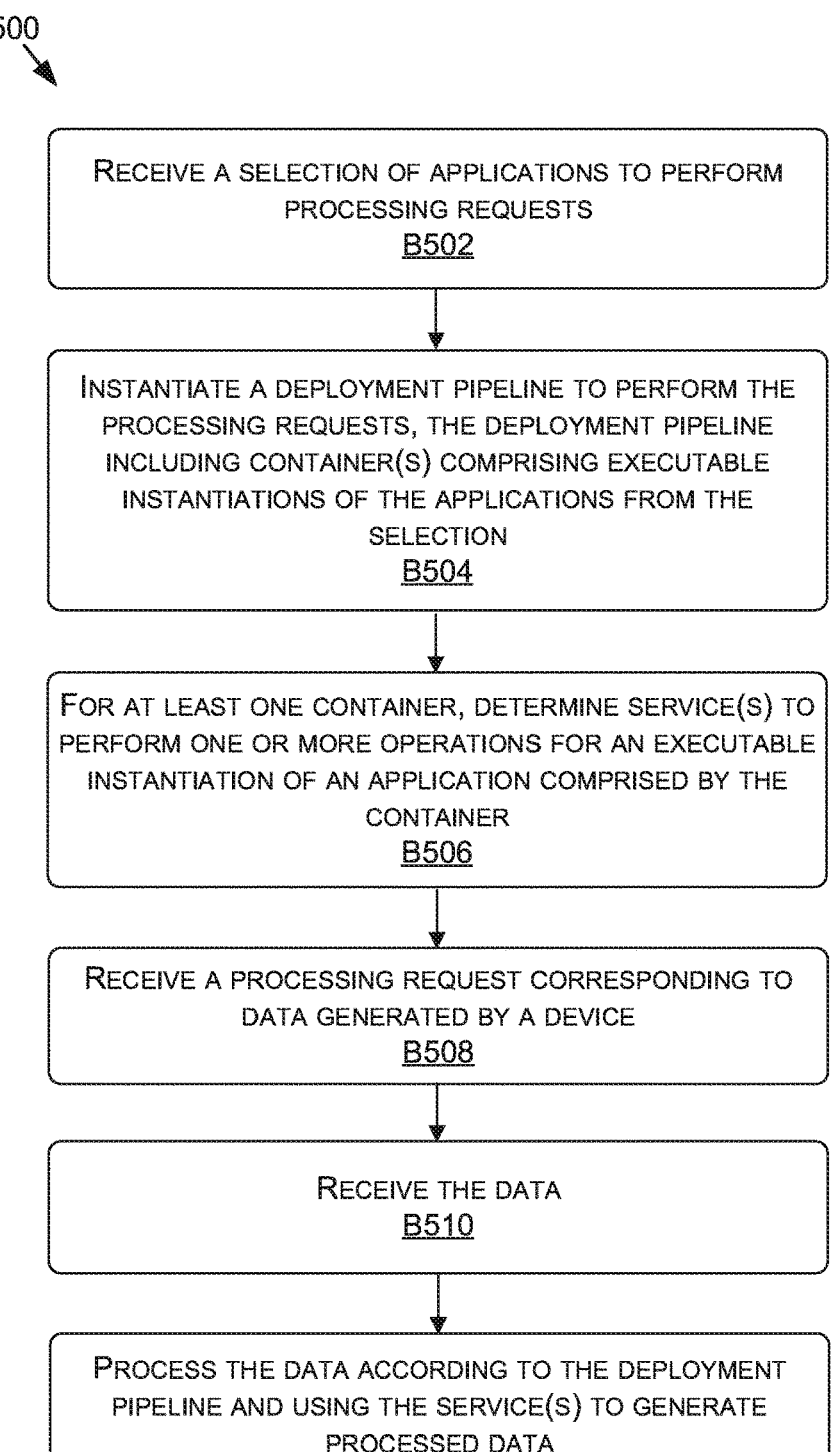

RECEIVE A SELECTION OF APPLICATIONS TO PERFORM PROCESSING REQUESTS
B502

INSTANTIATE A DEPLOYMENT PIPELINE TO PERFORM THE PROCESSING REQUESTS, THE DEPLOYMENT PIPELINE INCLUDING CONTAINER(S) COMPRISING EXECUTABLE INSTANTIATIONS OF THE APPLICATIONS FROM THE SELECTION
B504

FOR AT LEAST ONE CONTAINER, DETERMINE SERVICE(S) TO PERFORM ONE OR MORE OPERATIONS FOR AN EXECUTABLE INSTANTIATION OF AN APPLICATION COMPRISED BY THE CONTAINER
B506

RECEIVE A PROCESSING REQUEST CORRESPONDING TO DATA GENERATED BY A DEVICE
B508

RECEIVE THE DATA
B510

PROCESS THE DATA ACCORDING TO THE DEPLOYMENT PIPELINE AND USING THE SERVICE(S) TO GENERATE PROCESSED DATA
B512

FIGURE 5

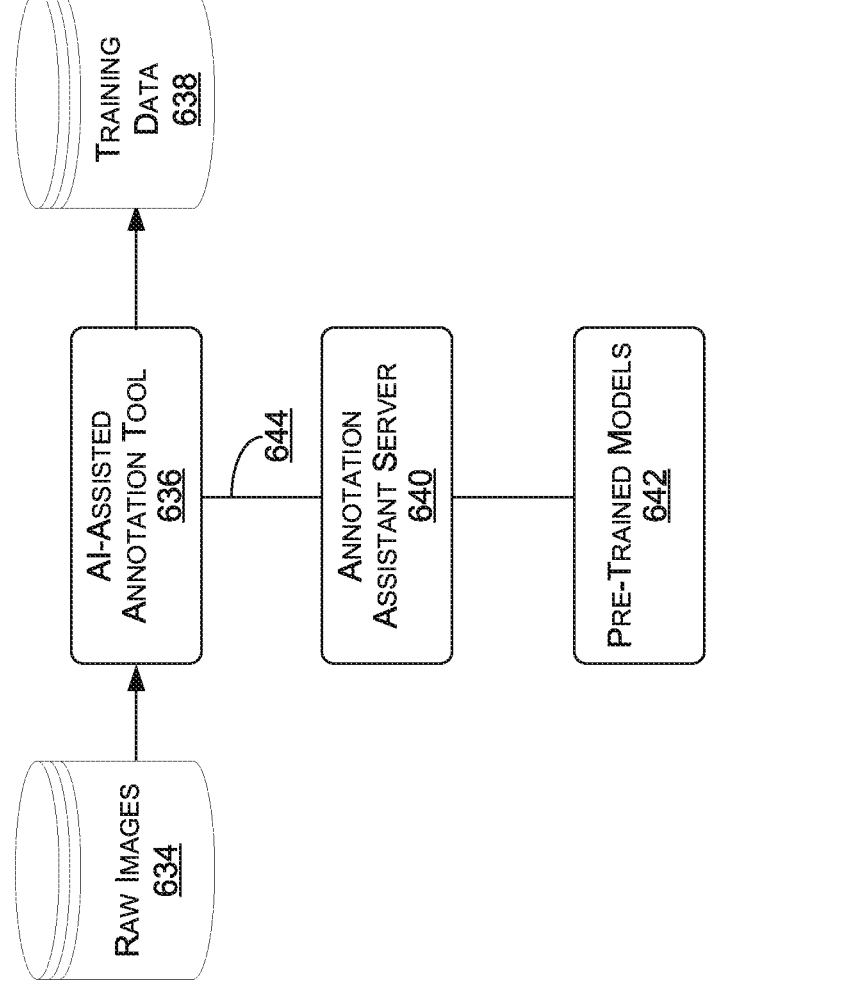
FIGURE 6C

700

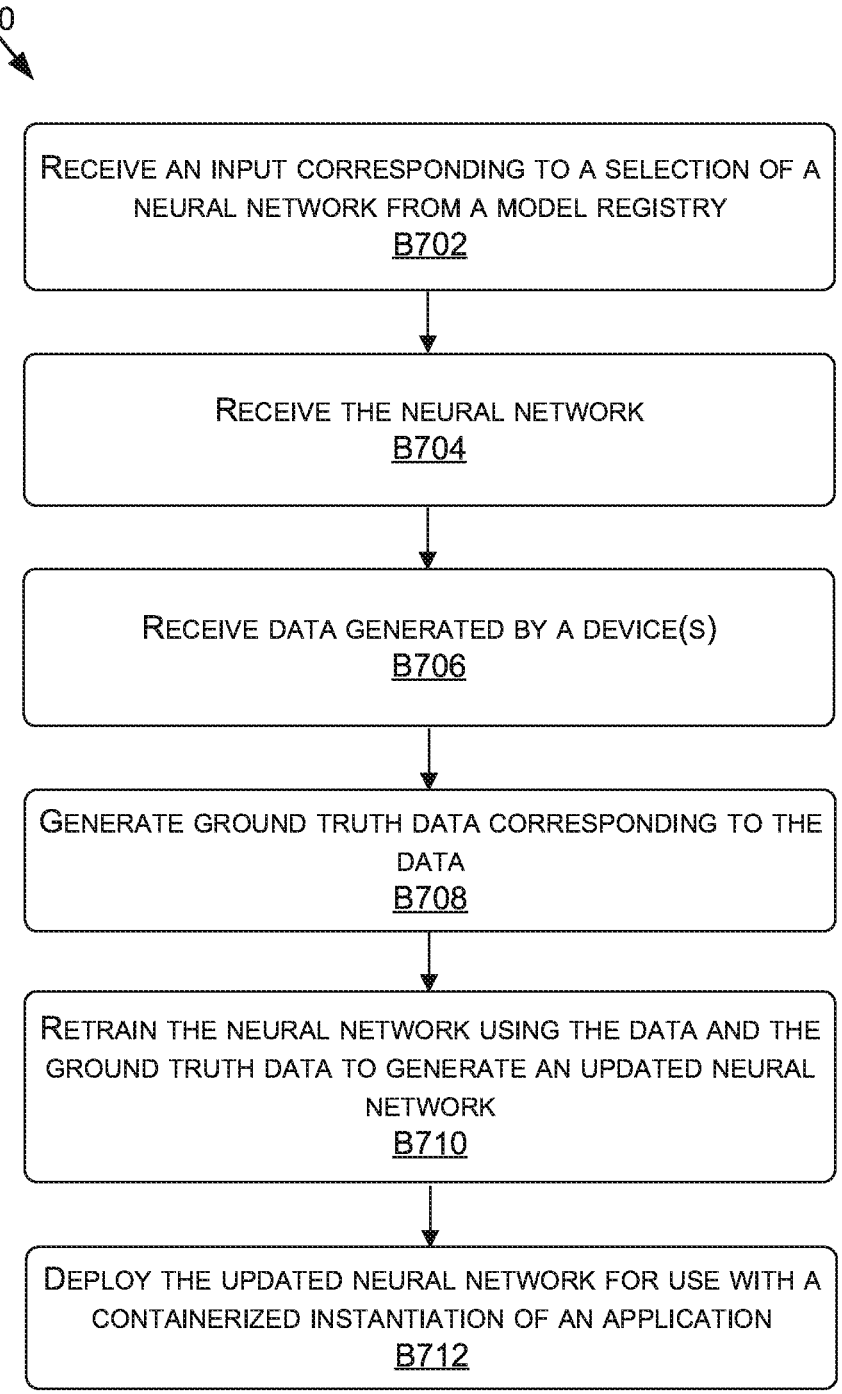

RECEIVE AN INPUT CORRESPONDING TO A SELECTION OF A NEURAL NETWORK FROM A MODEL REGISTRY
B702

RECEIVE THE NEURAL NETWORK
B704

RECEIVE DATA GENERATED BY A DEVICE(S)
B706

GENERATE GROUND TRUTH DATA CORRESPONDING TO THE DATA
B708

RETRAIN THE NEURAL NETWORK USING THE DATA AND THE GROUND TRUTH DATA TO GENERATE AN UPDATED NEURAL NETWORK
B710

DEPLOY THE UPDATED NEURAL NETWORK FOR USE WITH A CONTAINERIZED INSTANTIATION OF AN APPLICATION
B712

MEMORY
804

I/O PORT(S)
812

CPU(S)
806

I/O COMPONENTS
814

GPU(S)
808

POWER SUPPLY
816

COMM. INTERFACE
810

PRESENTATION
COMPONENT(S)
818

802

VIRTUALIZED COMPUTING PLATFORM FOR INFERENCING, ADVANCED PROCESSING, AND MACHINE LEARNING APPLICATIONS

CROSS-REFERENCE TO RELATED APPLICATIONS

This application claims the benefit of U.S. Provisional Application No. 62/700,071, filed on Jul. 18, 2018 and U.S. Provisional Application No. 62/820,188, filed Mar. 18, 2019, which are hereby incorporated by reference in their entirety.

BACKGROUND

Throughout recent history, imaging operations have been integral to research and diagnostics in a wide variety of industries, healthcare and medical research being among them. Medical imaging devices—such as computed tomography (CT) scan machines, positron emission technology (PET) scan machines, nuclear imaging machines, X-ray machines, ultrasound machines, and magnetic resonance imaging (MRI) machines—are widely used to aid medical professions and data scientists in visualizing a subject's anatomy for identifying anomalies, determining diagnoses, and researching organ function and disease. Modern, well-equipped hospitals and labs may have any number of these medical imaging devices on-premises. As innovations in computing—and especially graphics processing—have advanced, graphics processing units (GPUs) have increasingly been used in medical imaging devices to improve their performance and functionality.

Despite these advances in technology, a healthcare or medical practitioner is still required to perform accurate diagnoses—often relying on each practitioner's perception, understanding, and specific experience. In some instances, machine learning—e.g., using deep neural networks (DNNs)—has been used to capture these perceptions of on-premises practitioners to perform classification, segmentation, and object detection tasks in the medical imaging field. However, building, training, deploying, and executing machine learning to perform these tasks is exceedingly complex and difficult, typically requiring extensive and costly upgrades to the computing infrastructure. As a result, it may be prohibitively expensive or time-consuming to deploy on hospital premises. In addition, because various machine learning tasks—e.g., classification, segmentation, reconstruction, etc.—may each be a responsibility of a different team at an individual hospital, collaboration and integration between the various tasks may increase the complexity of deployment on-premises.

Moreover, computing capabilities for medical imaging devices are often capped years before the devices are available for shipment. For this reason, the technology being used at hospitals is often at least a few years outdated, creating a latency or gap between cutting edge medical imaging technology that is actually available and the current install base of medical imaging devices in clinics and hospitals. This latency or gap carries over to the machine learning capabilities of a hospital, as the programming and training of the machine learning models is created and deployed for use with already outdated medical imaging devices. As a result, as more accurate imaging techniques and devices are developed, in addition to more optimized and informative machine learning models, hospitals are constrained to the technology of their current medical imaging devices— thereby reducing the ability of the hospital to provide the most accurate and informative diagnoses and treatment of patients.

SUMMARY

Embodiments of the present disclosure relate to a virtualized computing platform for inferencing, advanced processing, and machine learning. Systems and methods are disclosed that allow for customized inference or processing pipelines by selecting, organizing, and/or adapting container hosted applications for local, on-premise implementations. In embodiments, machine learning models that may be trained, updated, and/or generated at a first facility may be leveraged and updated for location specific implementation to perform image processing and/or inferencing operations at a second, different facility.

In contrast to conventional systems, such as those described above, the system of the present disclosure accelerates inferencing, imaging operations, and informatics while minimizing the complexity of on-premise compute infrastructure requirements. For example, a virtual computing platform that continually adapts to new advancements in technology may be used to improve patient care through advanced diagnostics and research. The system allows for selection, organization, and deployment of containers—hosting instantiations of applications—in inference and/or image deployment pipelines. The pipelines may be configured for receiving (for example, medical) imaging data, processing the data, and outputting meaningful and informative results to practitioners. As such, because the pipelines may be dynamically customizable, outputs of imaging devices, radiology devices, gene sequencing devices, genomics devices, and/or processing devices may be used by updated, state-of-the-art technology within the virtualized platform to provide accurate and efficient results while reducing the burden of deployment on-premise as compared to conventional approaches.

In addition, within various containers, machine learning models may be deployed for image inferencing and training. In contrast to conventional systems, the machine learning models that are deployed may be selected from a remote database of existing machine learning models. As these existing machine learning models are deployed and updated at various locations, a crowd sourcing approach may be used to generate more universal machine learning models for simplifying and expediting deployment across locations. By training and/or updating the machine learning models on-premise, at various locations, the confidentiality of patient records—in view of state and federal laws and regulations (e.g., the Health Insurance Portability and Accountability Act (HIPAA)) for the handling and use of patient information—may be maintained while more robust and accurate machine learning models may be generated. Further, by providing existing machine learning models, the compute resources, expense, and time required for local, on-premise creation, training, and deployment of machine learning models is drastically reduced, and the resulting models may be better optimized for their respective applications.

BRIEF DESCRIPTION OF THE DRAWINGS

The present systems and methods for a virtualized computing platform for image inferencing in medical applications is described in detail below with reference to the attached drawing figures, wherein:

FIG. 5 is a flow diagram showing a method for deploying an advanced computing pipeline in accordance with some embodiments of the present disclosure;

FIG. 6C is an example illustration of a client-server architecture to enhance annotation tools with pre-trained annotation models, in accordance with some embodiments of the present disclosure;

FIG. 7 is a flow diagram showing a method 700 for using transfer learning to train a machine learning model for deployment in an advanced computing pipeline, in accordance with some embodiments of the present disclosure.

DETAILED DESCRIPTION

Systems and methods are disclosed related a virtualized computing platform for advanced computing, such as image inferencing and image processing in medical applications. Without limitation, the medical imaging modalities used within the systems of the present disclosure may include radiography, magnetic resonance imaging (MRI), nuclear medicine, ultrasound, sonography, elastography, photoacoustic imaging, tomography, echocardiography, functional near-infrared spectroscopy, and magnetic particle imaging, or the combination of any of these modalities. Although primarily described herein with respect to medical imaging operations, the virtualized computing platform and associated processes described herein may additionally or alternatively be used, without limitation, in forensic science analysis, sub-surface detection and imaging (e.g., oil exploration, archaeology, paleontology, etc.), topography, oceanography, geology, osteology, meteorology, intelligent area or object tracking and monitoring, sensor data processing (e.g., RADAR, SONAR, LIDAR, etc.), and/or genomics and gene sequencing.

Figure 1:
FIG. 1 is an example data flow diagram for an advanced computing pipeline, in accordance with some embodiments of the present disclosure.

With reference to FIG. 1, FIG. 1 is an example data flow diagram for a process 100 of generating and deploying an image processing and inferencing pipeline, in accordance with some embodiments of the present disclosure. The process 100 may be deployed for use with imaging devices, processing devices, genomics devices, gene sequencing devices, radiology devise, and/or other device types at one or more facilities 102, such as medical facilities, hospitals, healthcare institutes, clinics, research or diagnostic labs, and/or the like. Additionally, or alternatively, the process may be deployed to perform genomics analysis and inferencing on sequencing data. Examples of genomic analyses that may be performed using the systems and processes described herein include, without limitation, variant calling, mutation detection, and gene expression quantification. The process 100 may be executed within a training system 104 and/or a deployment system 106. The training system 104 may be used to perform training, deployment, and implementation of machine learning models (e.g., neural networks, object detection algorithms, computer vision algorithms, etc.) for use in the deployment system 106. The deployment system 106 may be configured to offload processing and compute resources among a distributed computing environment to reduce the infrastructure requirements at the facility 102. In addition, the deployment system 106 may provide a streamlined platform for selecting, customizing, and implementing virtual instruments for use with imaging devices (e.g., MRI, CT Scan, X-Ray, Ultrasound, etc.) or sequencing devices at the facility 102. The virtual instruments may include software-defined applications for performing one or more processing operations with respect to imaging data generated by the imaging devices, sequencing devices, radiology devices, and/or other device types. One or more of the applications in the pipeline may use or call upon services (e.g., inference, visualization, compute, AI, etc.) of the deployment system 106 during execution of the applications. As such, because the services and/or the applications may be predefined by the deployment system 106, when implementing the advanced processing and inferencing pipeline at the facility 102, the process of implementation may be expedited, and may reduce infrastructure requirements as at least some of the processing and compute resources may be offloaded to the cloud, or to AI systems specifically designed for handling the application and/or service processing of the pipeline.

In some embodiments, some of the applications used in the advanced processing and inferencing pipelines may use machine learning models or other AI to perform one or more processing steps. The machine learning models may be trained at the facility 102 using data 108 (such as imaging data) generated at the facility 102 (and stored on one or more picture archiving and communication system (PACS) servers at the facility 102), may be trained using imaging or sequencing data 108 from another facility(ies) (e.g., a different hospital, lab, clinic, etc.), or a combination thereof. In either example, the training system 104 may be used to provide applications, services, and/or other resources for generating working, deployable machine learning models for the deployment system 106.

A model registry 124 may be backed by object storage that may support versioning and object metadata. The object storage may be accessible through, for example, a cloud storage (e.g., cloud 226 of FIG. 2) compatible application programming interface (API) from within the cloud platform. The machine learning models within the model registry 124 may uploaded, listed, modified, or deleted by developers or partners of the system interacting with the API. In addition, the API may provide access to methods that allow users with appropriate credentials to associate models with applications, such that the models may be executed as part of the execution of the containerized instantiations of the applications.

A first example of a training pipeline 204 (FIG. 2) may include a scenario where the facility 102 is training their own machine learning model, or has an existing machine learning model that needs to be optimized or updated. In such an example, the imaging data 108 generated by the imaging device(s), sequencing devices, and/or other device types may be received. Once the imaging data 108 is received, AI-assisted annotation 110 may be used (e.g., as described at least with respect to FIG. 6B) to aid in generating annotations corresponding to the imaging data 108 to be used as ground truth data for the machine learning model. The AI-assisted annotation 110 may include one or more machine learning models (e.g., convolutional neural networks (CNNs)) that may be trained to generate annotations corresponding to certain types of imaging data 108 (e.g., from certain devices) and/or certain types of anomalies in the imaging data 108. The AI-assisted annotations 110 may then be used directly, or may be adjusted or fine-tuned using an annotation tool (e.g., by a researcher, a clinician, a doctor, a scientist, etc.), to generate the ground truth data. In addition, in some examples, labeled clinic data 112 (e.g., annotations provided by a clinician, doctor, scientist, technician, etc.) may be used as ground truth data for training the machine learning model. As such, the AI-assisted annotations 110, the labeled clinic data 112, or a combination thereof may be used as ground truth data for training the machine learning model. The trained machine learning model may be referred to as the output model 116, and may be used by the deployment system 106, as described herein.

A second example of a training pipeline 204 (FIG. 2) may include a scenario where the facility 102 needs a machine learning model for use in performing one or more processing tasks for one or more applications in the deployment system 106, but the facility 102 may not currently have such a machine learning model (or may not have a model that is optimized, efficient, or effective for such purposes). In such an example, an existing machine learning model may be selected from a model registry 124. For example, the model registry 124 may include machine learning models trained to perform a variety of different inference tasks on imaging data. The machine learning models in the model registry 124 may have been trained on imaging data from different facilities than the facility 102 (e.g., facilities remotely located). For example, the machine learning models may have been trained on imaging data from one location, two locations, or any number of locations. In such an example, when being trained on imaging data from a specific location, the training may take place at that location, or at least in a manner that protects the confidentiality of the imaging data or restricts the imaging data from being transferred off-premises (e.g., to comply with HIPAA regulations, privacy regulations, etc.). As such, once the model is trained—or partially trained—at one location, the machine learning model may be added to the model registry 124. In some embodiments, the machine learning model may then be retrained, or updated, at any number of other facilities, and the retrained or updated model may be made available in the model registry 124. A machine learning model may then be selected from the model registry 124—and referred to as the output model 116—and may be used in the deployment system 106 to perform the one or more processing tasks for one or more applications of the deployment system.

As another, third example of a training pipeline 204 (FIG. 2), a scenario may include the facility 102 requiring a machine learning model for use in performing one or more processing tasks for one or more applications in the deployment system 106, but the facility 102 may not currently have such a machine learning model (or may not have a model that is optimized, efficient, or effective for such purposes). However, different from the second example above, the machine learning model selected from the model registry 124 may not be fine-tuned or optimized for the imaging data 108 generated at the facility 102. This may be a result of differences in populations, genetic variations, robustness of the training data used to train the machine learning model, diversity in anomalies of training data, and/or other issues with the training data. As such, AI-assisted annotation 110 may be used (e.g., as described at least with respect to FIG. 6B) to aid in generating annotations corresponding to the imaging data 108 to be used as ground truth data for retraining or updating the machine learning model. In addition, in some examples, labeled clinic data 112 (e.g., annotations provided by a clinician, doctor, scientist, etc.) may be used as ground truth data for training the machine learning model. This process of retraining or updating the machine learning model may be referred to as model training 114. As such, model training 114—e.g., the AI-assisted annotations 110, the labeled clinic data 112, or a combination thereof—may be used as ground truth data for retraining or updating the machine learning model. The trained machine learning model may be referred to as the output model 116, and may be used by the deployment system 106, as described herein.

The deployment system 106 may include software 118, services 120, hardware 122, and/or other components, features, and functionality. The deployment system 106 may include a software "stack," such that the software 118 may be built on top of the services 120 and may use the services 120 to perform some or all of the processing tasks, and the services 120 and the software 118 may be built on top of the hardware 122 and use the hardware 122 to execute the processing, storage, and/or other compute tasks of the deployment system 106. The software 118 may include any number of different containers, where each container may execute an instantiation of an application. Each application may perform one or more processing tasks in an advanced processing and inferencing pipeline (e.g., inferencing, object detection, feature detection, segmentation, image enhancement, calibration, etc.). As such, for each type of imaging device (e.g., CT, MRI, X-Ray, ultrasound, sonography, echocardiography, etc.), sequencing device, radiology device, genomics device, etc., there may be any number of containers that may perform a data processing task with respect to imaging data 108 (or other data types, such as those described herein) generated by the device. The advanced processing and inferencing pipeline may be defined based on selections of different containers that are desired or required for processing the imaging data 108, in addition to containers that receive and configure the imaging data for use by each of the containers and/or for use by the facility 102 after processing through the pipeline (e.g., to convert the outputs back to a usable data type, such as digital imaging and communications in medicine (DICOM) data, radiology information system (RIS) data, clinical information system (CIS) data, remote procedure call (RPC) data, data substantially compliant with a representation state transfer (REST) interface, data substantially compliant with a file-based interface, and/or raw data, for storage and display at the facility 102). For a device type, the combination of the containers within the software 118 (e.g., that make up the pipeline) may be referred to as a virtual instrument (as described in more detail herein), and the virtual instrument may leverage the services 120 and the hardware 122 to execute some or all of the processing tasks of the applications instantiated in the containers.

An data processing pipeline may receive input data (e.g., the imaging data 108) in a DICOM, RIS, CIS, REST compliant, RPC, raw, and/or other format in response to an inference request (e.g., a request from a user of the deployment system 106, such as a clinician, a doctor, a radiologist, etc.). The input data may be representative of one or more images, video, and/or other data representations generated by one or more imaging devices, sequencing devices, radiology devices, genomics devices, and/or other device types. In some examples, the data may undergo pre-processing as part of the data processing pipeline to prepare the data for processing by one or more applications. In addition, post-processing may be performed on the output of one or more inferencing tasks or other processing tasks of the pipeline to prepare the output data for a next application and/or to prepare the output data for transmission and/or use by the user (e.g., as a response to the inference request). The inferencing tasks may be performed by one or more machine learning models, such as trained or deployed neural networks, which may include the output models 116 of the training system 104.

The tasks of the data processing pipeline may be encapsulated in a container(s) that each represent a discrete, fully functional instantiation of an application and virtualized computing environment that is able to reference the machine learning models. As such, the containers or applications may be published into a private (e.g., limited access) area of a container registry (described in more detail herein), and the trained or deployed models may be stored in the model registry 124 and associated with one or more applications. For example, images of the applications (e.g., container images) may be available in the container registry, and once selected by a user from the container registry for deployment in a pipeline, the image may be used to generate a container for an instantiation of the application for use by the user's system.

Developers (e.g., software developers, clinicians, doctors, etc.) may develop, publish, and store applications (e.g., as containers) for performing image processing and/or inferencing on supplied data. The development, publishing, and/or storing may be performed using a software development kit (SDK) associated with the system (e.g., to ensure that the application and/or container developed is compliant with or compatible with the system). The application that is developed may be tested locally (e.g., at a first facility, on data from the first facility) with the SDK which may support at least some of the services 120 as the system (e.g., the system 200 of FIG. 2). Because DICOM objects may contain anywhere from one to hundreds of images or other data types, and due to the variation in data, the developer may be responsible for managing (e.g., setting constructs for, building pre-processing into the application, etc.) extraction and preparation of incoming DICOM data. Once validated by the system 200 (e.g., for accuracy, safety, patient privacy, etc.), the application may be available in a container registry for selection and/or implementation by a user (e.g., a hospital, clinic, lab, healthcare provider, etc.) to perform one or more processing tasks with respect to data at a facility (e.g., a second facility) of the user.

Figure 2:
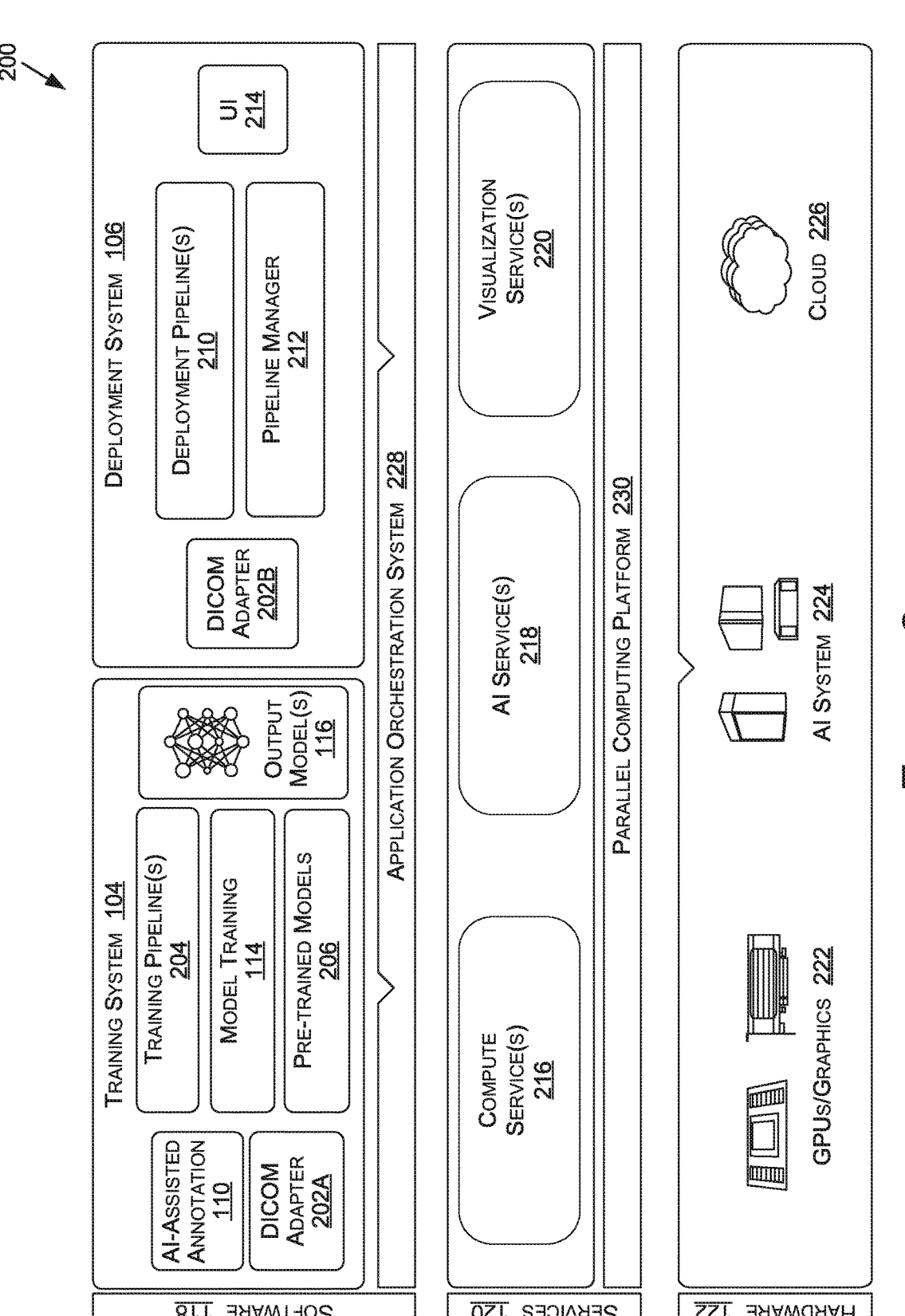
FIG. 2 is a system diagram for an example system for training, adapting, instantiating and deploying machine learning models in an advanced computing pipeline, in accordance with some embodiments of the present disclosure.

The developers may then share the applications or containers through a network for access and use by users of the system (e.g., the system 200 of FIG. 2). Once shared, the completed and validated applications or containers may be stored in the container registry and the associated machine learning models may be stored in the model registry 124. As such, a requesting entity (e.g., a user at a medical facility)—who provides an inference or image processing request— may browse the container registry and/or the model registry 124 for an application, container, dataset, machine learning model, etc., select the desired combination of elements for inclusion in the data processing pipeline, and submit an imaging processing request. The request may include the input data (and associated patient data, in some examples) that is necessary to perform the request, and/or may include a selection of the application(s) and/or machine learning models to be executed in processing the request. The request may then be passed to one or more components of the deployment system 106 (e.g., the cloud) to perform the processing of the data processing pipeline. The processing by the deployment system 106 may include referencing the selected elements (e.g., applications, containers, models, etc.) from the container registry and/or the model registry 124. Once the results are generated by the pipeline, the results may be returned to the user for reference (e.g., for viewing in a viewing application suite executing on a local, on-premises workstation or terminal). As a non-limiting example, a radiologist may receive results from an data processing pipeline including any number of application and/or containers, where the results may include anomaly detection in X-rays, CT scans, MRIs, and/or the like.

To aid in the processing or execution of the applications or containers in the pipelines, the services 120 may be leveraged. The services 120 may include compute services, artificial intelligence (AI) services, visualization services, and/or other service types. The services 120 may provide functionality that is common to one or more of the applications in the software 118, so the functionality may be abstracted to a service that may be called upon or leveraged by the applications. In doing so, the functionality provided by the services 120 may run dynamically and more efficiently, while also scaling well by allowing applications to process data in parallel (e.g., using a parallel computing platform 230 (FIG. 2)). For example, rather than each application that shares the same functionality offered by a service 120 being required to have a respective instance of the service 120, the service 120 may be shared between and among the various applications. The services may include an inference server or engine that may be used for executing detection or segmentation tasks, as non-limiting examples. A model training service may be included that may provide machine learning model training and/or retraining capabilities. A data augmentation service may further be included that may provide GPU accelerated data (e.g., DICOM, RIS, CIS, REST compliant, RPC, raw, etc.) extraction, resizing, scaling, and/or other augmentation. A visualization service may be used that may add image rendering effects—such as ray-tracing, rasterization, denoising, sharpening, etc.—to add realism to two-dimensional (2D) and/or three-dimensional (3D) models. Virtual instrument services may be included that provide for beam-forming, segmentation, inferencing, imaging, and/or support for other applications within the pipelines of the virtual instruments.

As an example, where a service 120 includes an AI service (e.g., an inference service), one or more machine learning models associated with an application for anomaly detection (e.g., tumors, growth abnormalities, scarring, etc.) may be executed by calling upon (e.g., as an API call) the inference service (e.g., an inference server) to execute the machine learning model(s), or the processing thereof, as part of the application execution. Similarly, where another application includes one or more machine learning models for segmentation tasks, the application may call upon the inference service to execute the machine learning models for performing one or more of the processing operations associated with the segmentation tasks. As such, the software 118 implementing the advanced processing and inferencing pipeline that includes the segmentation application and the anomaly detection application may be streamlined because each of the applications may call upon the same inference service to perform one or more inferencing tasks.

The hardware 122 may include GPUs, CPUs, graphics cards, an AI/deep learning system (e.g., an AI supercomputer, such as NVIDIA's DGX), a cloud platform, or a combination thereof. For example, these different types of the hardware 122 may be used to provide efficient, purpose-built support for the software 118 and the services 120 in the deployment system 106. For example, the use of GPU processing may be implemented for processing locally (e.g., at the facility 102), within the AI/deep learning system, in the cloud, and/or in other processing components of the deployment system 106 to improve efficiency, accuracy, and efficacy of image processing, image reconstruction, segmentation, MRI exams, stroke or heart attack detection (e.g., in real-time), image quality in rendering, and/or the like. A well-equipped facility may include imaging devices, genomics devices, sequencing devices, and/or other device types on-premises that may leverage the GPUs to generate imaging data representative of a subject's anatomy. In addition, the software 118 and/or services 120 may be optimized for GPU processing with respect to deep learning, machine learning, and/or high performance computing, as non-limiting examples. In some embodiments, at least some of the computing environment of the deployment system 106 and/ or the training system 104 may be executed in a datacenter one or more supercomputers or high performance computing systems, with GPU optimized software (e.g., the hardware and software combination of NVIDIA's DGX System). These datacenters may be compliant with the provisions of HIPAA, such that the receipt, processing, and transmission of imaging data and/or other patient data is securely handled with respect to the privacy of patient data. In addition, the hardware 122 may include any number of GPUs that may be called upon to perform processing of data in parallel, as described herein. The cloud platform may further include GPU processing for GPU-optimized execution of deep learning tasks, machine learning tasks, or other computing tasks. In some examples, the cloud platform (e.g., NVIDIA's NGC) may be executed using an AI/deep learning supercomputer(s) and/or GPU-optimized software (e.g., as provided on NVIDIA's DGX Systems) as a hardware abstraction and scaling platform. As such, the cloud platform may integrate an application container clustering system or orchestration system (e.g., KUBERNETES) on multiple GPUs to enable seamless scaling and load balancing.

Now referring to FIG. 2, FIG. 2 is a system diagram for an example system 200 for generating and deploying an imaging deployment pipeline, in accordance with some embodiments of the present disclosure. It should be understood that this and other arrangements described herein are set forth only as examples. Other arrangements and elements (e.g., machines, interfaces, functions, orders, groupings of functions, etc.) may be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by entities may be carried out by hardware, firmware, and/or software. For instance, various functions may be carried out by a processor executing instructions stored in memory.

The system 200 may be used to implement the process 100 of FIG. 1 and/or other processes including advanced processing and inferencing pipelines. The system 200 may include the training system 104 and the deployment system 106. Although illustrated as part of the software 118, the training system 104 and the deployment system 106 may be implemented using the software 118, the services 120, and/or the hardware 122, as described herein.

In some embodiments, the system 200 (e.g., the training system 104 and/or the deployment system 106) may implemented in a cloud computing environment (e.g., using the cloud 226). In other embodiments, the system 200 may be implemented locally with respect to a healthcare services facility, or as a combination of both cloud and local computing resources. As described herein, in embodiments where cloud computing is implemented, the patient data may be separated from, or unprocessed by, by one or more components of the system 200 that would render the processing non-compliant with HIPAA and/or other data handling and privacy regulations or laws. For example, access to the APIs in the cloud 226 may be restricted to authorized users through enacted security measures or protocols. One example of a security protocol may include web tokens that may be signed by an authentication (e.g., AuthN, AuthZ, Gluecon, etc.) service and may carry appropriate authorization. In addition, the APIs of the virtual instruments (described herein), or other instantiations of the system 200, may be restricted to a set of public IPs that have been vetted or authorized for interaction.

The various components of the system 200 may communicate between and among one another using any of a variety of different network types, including but not limited to local area networks (LANs) and/or wide area networks (WANs) via wired and/or wireless communication protocols. In addition, communication between facilities and components of the system 200 (e.g., for transmitting inference requests, for receiving results of inference requests, etc.) may be communicated over data bus(ses), wireless data protocols (Wi-Fi), wired data protocols (e.g., Ethernet), and/or the like.

The training system 104 may execute training pipelines 204, similar to those described herein with respect to FIG. 1. For example, where one or more machine learning models are to be used in the deployment pipelines 210 by the deployment system 106, the training pipelines 204 may be used to train or retrain one or more (e.g. pre-trained) models, and/or implement one or more of the pre-trained models 206 (e.g., without a need for retraining or updating). As a result of the training pipelines 204, the output model(s) 116 may be generated. The training pipelines 204 may include any number of processing steps, such as but not limited to imaging data (or other input data) conversion or adaption (e.g., using DICOM adapter 202A to convert the DICOM images to another format suitable for processing by respective machine learning models, such as Neuroimaging Informatics Technology Initiative (NIfTI) format), AI-assisted annotation 110, labeling or annotating of the imaging data 108 to generate the labeled clinic data 112, model selection from a model registry, model training 114, training, retraining, or updating models, and/or other processing steps. In some embodiments, for different machine learning models used by the deployment system 106, different training pipelines 204 may be used. For example, the training pipeline 204 similar to the first example described with respect to FIG. 1 may be used for a first machine learning model, the training pipeline 204 similar to the second example described with respect to FIG. 1 may be used for a second machine learning model, and the training pipeline 204 similar to the third example described with respect to FIG. 1 may be used for a third machine learning model. As such, any combination of the tasks within the training system 104 may be used depending on what is required for each respective machine learning model. In some instances, one or more of the machine learning models may already be trained and ready for deployment so the machine learning models may not undergo any processing by the training system 104, and may be implemented by the deployment system 106.

The output model(s) 116 and/or the pre-trained model(s) 206 may include any types of machine learning models depending on the implementation or embodiment. For example, and without limitation, the machine learning models used by the system 200 may include machine learning model(s) using linear regression, logistic regression, decision trees, support vector machines (SVM), Naïve Bayes, k-nearest neighbor (Knn), K means clustering, random forest, dimensionality reduction algorithms, gradient boosting algorithms, neural networks (e.g., auto-encoders, convolutional, recurrent, perceptrons, Long/Short Term Memory (LSTM), Hopfield, Boltzmann, deep belief, deconvolutional, generative adversarial, liquid state machine, etc.), and/or other types of machine learning models.

Figure 6A:
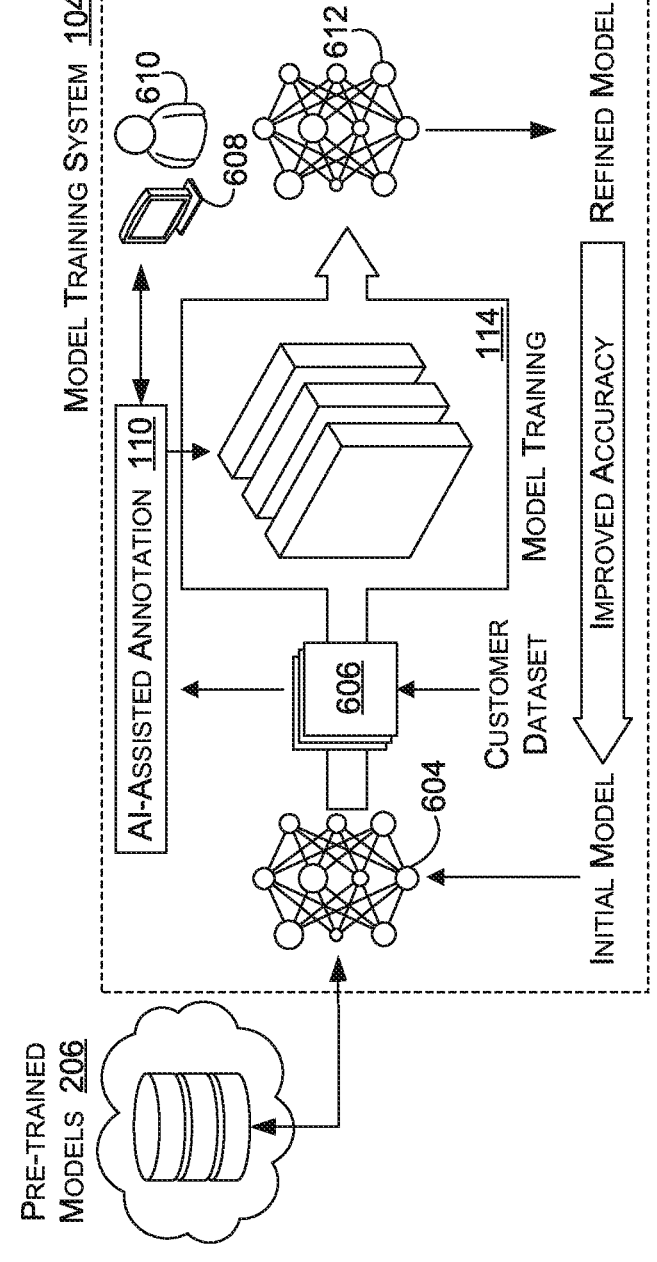
FIG. 6A illustrates a data flow diagram for a process to train a machine learning model, in accordance with some embodiments of the present disclosure.
Figure 6B:
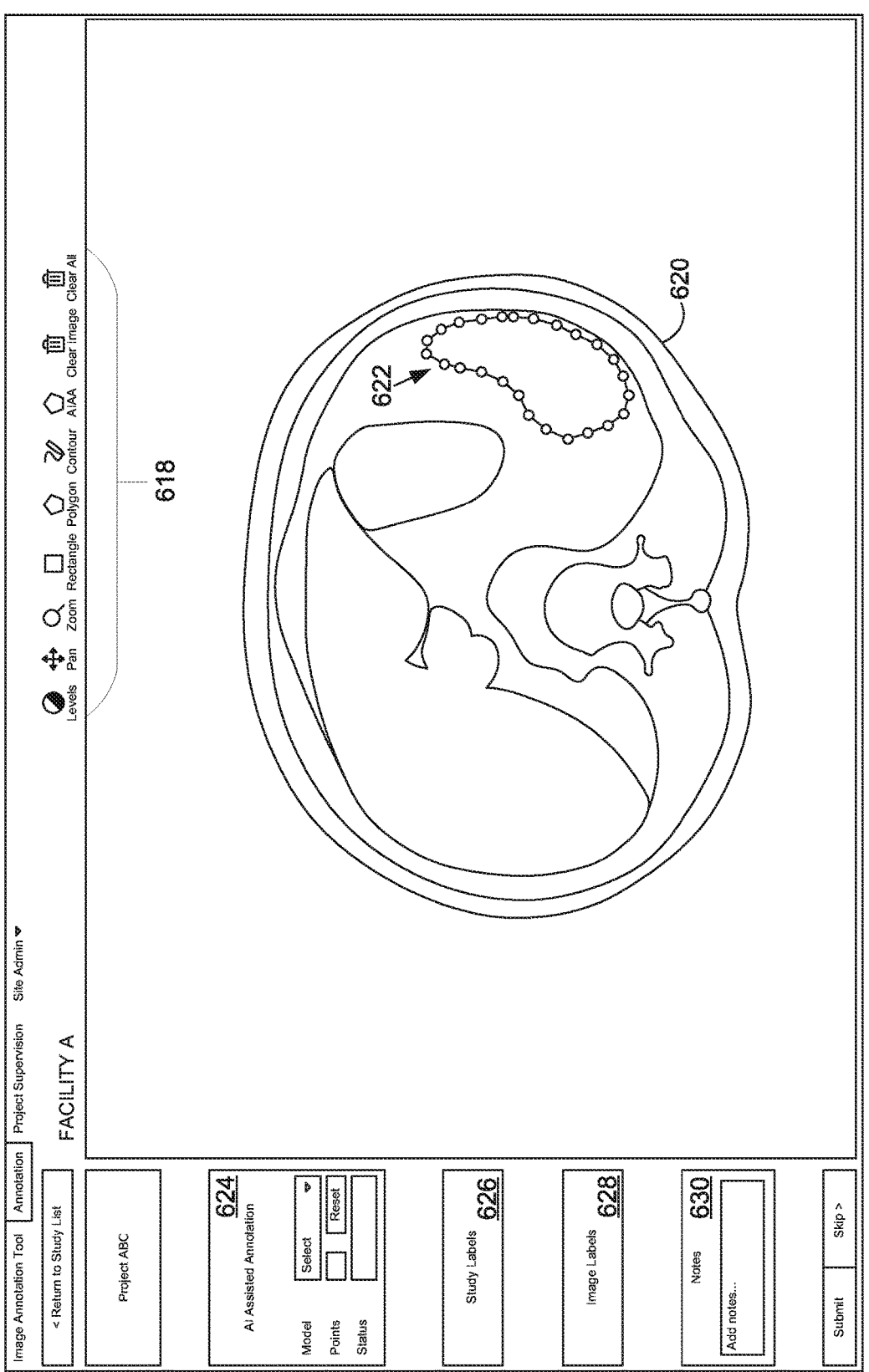
FIG. 6B is an example illustration of a graphical user interface for artificial intelligence assisted annotation, in accordance with some embodiments of the present disclosure.

The training pipelines 204 may include AI-assisted annotation, as described in more detail herein with respect to at least FIG. 6B and FIG. 6C. The labeled clinic data 112 (e.g., traditional annotation) may be generated by any number of techniques. For example, labels or other annotations may be generated within a drawing program (e.g., an annotation program), a computer aided design (CAD) program, a labeling program, another type of program suitable for generating the annotations or labels for ground truth, and/or may be hand drawn, in some examples. In any example, the ground truth data may be synthetically produced (e.g., generated from computer models or renderings), real produced (e.g., designed and produced from real-world data), machine-automated (e.g., using feature analysis and learning to extract features from data and then generate labels), human annotated (e.g., labeler, or annotation expert, defines the location of the labels), and/or a combination thereof. In some examples, for each instance of imaging data 108 (or other data type used by the machine learning models), there may be corresponding ground truth data generated by the training system 104. In one or more embodiments, AI-assisted annotation may be performed as part of the deployment pipelines 210; either in addition to, or in lieu of the AI-assisted annotation included in training pipelines 204. The system 200 may include a multi-layer platform that may include a software layer (e.g., the software 118) of diagnostic applications (or other application types) that may perform one or more medical imaging and diagnostic functions. The system 200 may be communicatively coupled to (e.g., via encrypted links) PACS server networks of one or more facilities. The system 200 may be configured to access and referenced data (e.g., DICOM data, RIS data, raw data, CIS data, REST compliant data, RPC data, raw data, etc.) from the PACS servers (e.g., via a DICOM adapter 202, or another data type adapter such as RIS, CIS, REST compliant, RPC, raw, etc.) to perform operations, such as training machine learning models, deploying machine learning models, image processing, inferencing, and/or other operations.

The software layer may be implemented as a secure, encrypted, and/or authenticated API through which applications or containers may be invoked (e.g., called) from an external environment(s) (e.g., the facility 102). The applications, in turn, may then call or execute one or more services 120 for performing compute, AI, or visualization tasks associated with the respective applications, and the software 118 and/or the services 120 may leverage the hardware 122 to perform the processing tasks in an effective and efficient manner.

The deployment system 106 may execute deployment pipelines 210. The deployment pipelines 210 may include any number of applications that may be sequentially, non-sequentially, or otherwise applied to the imaging data (and/or other data types) generated by imaging devices, sequencing devices, genomics devices, etc.—including AI-assisted annotation, as described above. For example, as described herein, a deployment pipeline 210 for an individual device may be referred to as a virtual instrument for the device (e.g., a virtual ultrasound instrument, a virtual CT scan instrument, a virtual sequencing instrument, etc.). In addition, for a single device, there may be more than one deployment pipeline 210 depending on the information desired from the data generated by the device. For example, where detections of anomalies are desired from an MRI machine, there may be a first deployment pipeline 210, and where image enhancement is desired from the output of the MRI machine, there may be a second deployment pipeline 210.

The applications available for the deployment pipelines 210 may include any application that may be used for performing processing tasks on imaging data or other data from devices. As some non-limiting examples, different applications may be responsible for image enhancement, segmentation, reconstruction, anomaly detection, object detection, feature detection, treatment planning, dosimetry, beam planning (or other radiation treatment procedures), and/or other analysis, image processing, or inferencing tasks. The deployment system 106 may define the constructs for each of the applications, such that users of the deployment system 106 (e.g., medical facilities, labs, clinics, etc.) may understand the constructs and adapt the applications for implementation within their respective facility. For example, an application for image reconstruction may be selected for inclusion in the deployment pipeline 210, but the data type generated by the imaging device may be different from the data type used within the application. As such, the DICOM adapter 202B (and/or a DICOM reader) or another data type adapter or reader (e.g., RIS, CIS, REST compliant, RPC, raw, etc.) may be used within the deployment pipeline 210 to convert the data to a form useable by the application within the deployment system 106. In some examples, access to DICOM, RIS, CIS, REST compliant, RPC, raw, and/or other data type libraries may be accumulated and pre-processed. This may include decoding, extracting, and/or performing any convolutions, color corrections, sharpness, gamma, and/or other augmentations to the data. In addition, DICOM, RIS, CIS, REST compliant, RPC, and/or raw data may be unordered and a pre-pass may be executed to organize or sort collected data. Because various applications may share common image operations, in some embodiments, a data augmentation library (e.g., as one of the services 120) may be used to accelerate these operations. In addition, to avoid the bottleneck of conventional processing approaches that rely on CPU processing, the parallel computing platform 230 may be used for GPU acceleration of these processing tasks.

As another example, the image reconstruction application may include a processing task that includes the use of a machine learning model. However, the user may desire to use their own machine learning model, or to select a machine learning model from the model registry 124. As such, the user may implement their own machine learning model or select a machine learning model for inclusion in the application for performing the processing task. The applications may thus be selectable and customizable, and by defining the constructs of the applications, the deployment and implementation of the applications for a particular user are presented as a more seamless user experience. In addition, by leveraging the other features of the system 200—such as the services 120 and the hardware 122—the deployment pipelines 210 may be even more user friendly, provide for easier integration, and produce more accurate, efficient, and timely results.

The deployment system 106 may include a user interface 214 (e.g., a graphical user interface, a web interface, and/or the like) that may be used to select applications for inclusion in the deployment pipeline(s) 210, arrange the applications, modify or change the applications or parameters or constructs thereof, use and interact with the deployment pipeline(s) 210 during set-up and/or deployment, and/or to otherwise interact with the deployment system 106. Although not illustrated with respect to the training system 104, the user interface 214 (or a different user interface) may be used for selecting models for use in the deployment system 106, for selecting models for training, or retraining, in the training system 104, and/or for otherwise interacting with the training system 104.

Figure 3:
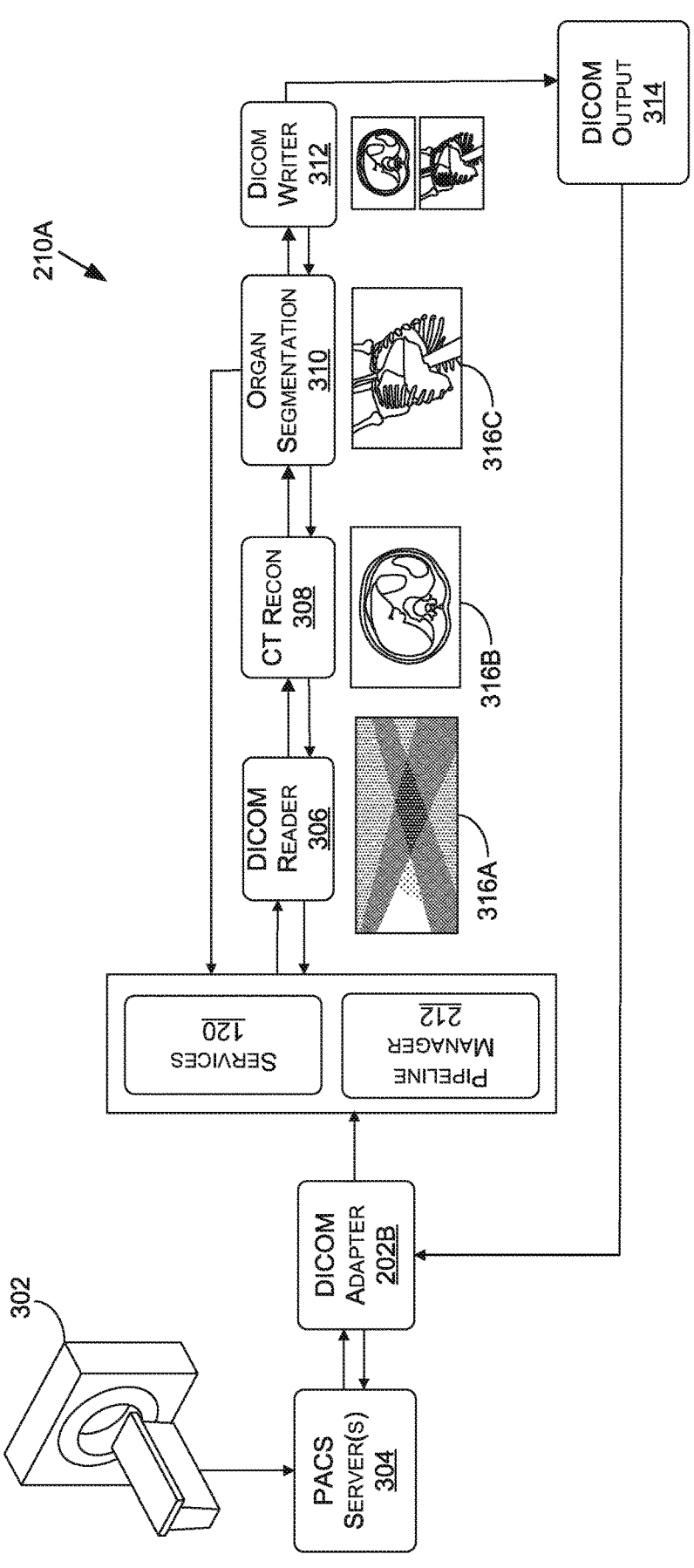
FIG. 3 includes an example illustration of an advanced computing pipeline 210A for processing imaging data, in accordance with some embodiments of the present disclosure.

A pipeline manager 212 may be used, in addition to an application orchestration system 228, to manage the interaction between the applications or containers of the deployment pipeline(s) 210 and the services 120 and/or the hardware 122. For example, the pipeline manager 212 may be configured to facilitate interactions from application to application, from application to service 120, and/or from application or service to hardware 122. Although illustrated as included in the software 118, this is not intended to be limiting, and in some examples (e.g., as illustrated in FIG. 3) the pipeline manager 212 may be included in the services 120. The application orchestration system 228 (e.g., Kubernetes, DOCKER, and/or the like) may include a container orchestration system that may group applications into containers as logical units for coordination, management, scaling, and deployment. By using containers for the applications, advantages over conventional virtualization techniques may be recognized. For example, by associating applications from the deployment pipeline(s) 210 (e.g., a reconstruction application, a segmentation application, etc.) with individual containers, each application may execute in a self-contained environment (e.g., at the kernel level) to increase speed and efficiency.

As such, each application and/or container (or image thereof) may be individually developed, modified, and deployed (e.g., a first user or developer may develop, modify, and deploy a first application and a second user or developer may develop, modify, and deploy a second application separate from the first user or developer). This may allow for focus on, and attention to, a task of a single application and/or container(s) without being hindered by the tasks of another application(s) or container(s). The interaction, communication, and cooperation between different containers or applications may be aided by the pipeline manager 212 and the application orchestration system 228. For example, so long as an expected input and/or output of each container or application is known by the system (e.g., based on the constructs of the applications or containers), the application orchestration system 228 and/or the pipeline manager 212 may facilitate the communication among and between, and sharing of resources among and between, each of the applications or containers. As such, because one or more of the applications or containers in the deployment pipeline(s) 210 may share the same services and resources, the application orchestration system 228 may orchestrate, load balance, and determine the sharing of the services or resources between and among the various applications or containers. For example, a scheduler may be used to track resource requirements of the applications or containers, current usage or planned usage of these resources, and the resource availability. The scheduler may thus allocate resources to the different applications and distribute the resources between and among the applications in view of the requirements and availability of the system. In some examples, the scheduler (and/or other component of the application orchestration system 228) may determine resource availability and distribution based on constraints imposed on the system (e.g., user constraints), such as quality of service (QoS), urgency of need for the data outputs (e.g., to determine whether to execute real-time processing or delayed processing), etc.

The services 120 leveraged by and shared by the applications or containers in the deployment system 106 may include compute services 216, AI services 218, visualization services 220, and/or other service types. For example, the applications may call (e.g., execute) one or more of the services 120 to perform processing operations for the application. The compute services 216 may be leveraged by the applications to perform super-computing or other high-performance computing (HPC) tasks. For example, the compute service(s) 216 may be leveraged to perform parallel processing (e.g., using a parallel computing platform 230) for processing data through one or more of the applications and/or one or more tasks of a single application, substantially simultaneously. The parallel computing platform 230 (e.g., NVIDIA's CUDA) may enable general purpose computing on GPUs (GPGPU) (e.g., GPUs 222). For example, a software layer of the parallel computing platform 230 may provide access to the virtual instruction sets and parallel computational elements of the GPUs, for the execution of compute kernels. The parallel computing platform 230 may include memory and, in some embodiments, the memory may be shared between and among multiple containers, and/or between and among different processing tasks within a single container. For example, inter-process communication (IPC) calls may be generated for multiple containers and/or for multiple processes within a container to use the same data from a shared segment of memory of the parallel computing platform 230 (e.g., where multiple different stages of an application or multiple applications are processing the same information). As a result, rather than making a copy of the data and moving the data to different locations in memory (e.g., a read/write operation), the same data in the same location of the memory may be used for any number of processing tasks (e.g., at a same time, at different times, etc.). In addition, as the data is used to generate new data as a result of processing, this information of the new location of the data may be stored and shared between the various applications. As such, the location of the data and the location of updated or modified data may be part of the definition of how the payload is understood within the containers.

The AI services 218 may be leveraged to perform inferencing services for executing machine learning model(s) associated with applications (e.g., tasked with performing one or more processing tasks of an application). For example, the AI services 218 may leverage the AI system 224 to execute the machine learning model(s) (e.g., neural networks, such as CNNs) for segmentation, reconstruction, object detection, feature detection, classification, and/or other inferencing tasks. For example, the applications of the deployment pipeline(s) 210 may use one or more of the output models 116 from the training system 104 and/or other models of the applications to perform inference on imaging data (e.g., DICOM data, RIS data, CIS data, REST compliant data, RPC data, raw data, etc.). With respect to the application orchestration system 228 (e.g., a scheduler), two or more categories of inferencing may be available. For example, a first category may include a high priority/low latency path that may achieve higher service level agreements, such as for performing inference on urgent requests during an emergency, or for a radiologist during diagnosis. As another example, a second category may include a standard priority path that may be used for requests that may be non-urgent or where analysis may be performed at a later time. As such, the application orchestration system 228 may distribute the resources (e.g., the services 120 and/or the hardware 122) based on the priority paths for the different inferencing tasks of the AI services 218.

In some embodiments, shared storage may be mounted to the AI services 218 within the system 200. The shared storage may operate as a cache (or other storage device type) and may be used to process inference requests from applications. For example, when an inference request is submitted, the request may be received by a set of API instances of the deployment system 106, and one of the instances may be selected (e.g., for best fit, for load balancing, etc.) to process the request. To process the request, the request may be entered into a database, the machine learning model may be located from the model registry 124 if not already in the cache, a validation step may ensure the appropriate machine learning model is loaded into the cache (e.g., the shared storage), and/or a copy of the model may be saved to the cache. In some examples, a scheduler (e.g., of the pipeline manager 212) may be used to launch an application that is referenced in the request if the application is not already running or if there are not enough instances of the application. In addition, if an inference server is not already launched to execute the model, the inference server may be launched. Any number of inference servers may be launched per model. For example, in a pull model, in which inference servers are clustered, models may be cached whenever load balancing is advantageous. In a push model, inference servers may be statically loaded in corresponding, distributed servers.

In some embodiments, inferencing may be performed using an inference server that runs in a container. An instance of the inference server may be associated with a model (and optionally a plurality of versions of the model). If an instance of an inference server does not exist when a request to perform inference on the model is received, a new instance may be loaded. When starting an inference server, a model may be passed to the inference server such that the same container may be used to serve different models so long as the inference server is running as a different instance.

During application execution, an inference request for a given application may be received, and the container (e.g., hosting an instance of an inference server) may be loaded (if not already), and a start procedure may be called. Preprocessing logic in the container may load, decode, and/or perform any additional pre-processing on the incoming data (e.g., using a CPU(s) and/or GPU(s)). Once the data is prepared for inference, the container may perform inference as necessary on the data. In some examples, this may include a single inference call on one image (e.g., a hand X-ray), or may require inference on hundreds of images (e.g., a chest CT). The application may summarize results before completing, which may include, without limitation, a single confidence score, pixel level-segmentation, voxel-level segmentation, generating a visualization, or generating text to summarize findings. In some embodiments, different models or applications may be assigned different priorities. For example, some models may have a real-time (TAT<1 min) priority while others may have lower priority (e.g., TAT<10 min). Model execution times may be measured from the requesting institution or entity and may include partner network traversal time, as well as execution on the inference service.

Transfer of requests between services 120 and inference applications may be hidden behind a software development kit (SDK), and robust transport may be provide through a queue. For example, a request will be placed in a queue via an API for an individual application/tenant ID combination and the SDK will pull the request from the queue and give the request to the application. The name of the queue may be provided in the environment from where the SDK will pick it up. As there may be many instances of an application, asynchronous communication through the queue may be useful as it may allow any instance of an application to pick up work as it becomes available. Results may be transferred back through the queue, to ensure no data is lost. Having queues may also provide the ability to segment work, as the highest priority work may go to the queue with the most instances of the application connected to it, while the lowest priority work may go to a queue with a single instance connected to it that processes tasks in the order received. In some embodiments, the application may run on a GPU-accelerated instance generated in the cloud 226, and the inference service may perform the actual inference on the GPU.

The visualization services 220 may be leveraged to generate visualizations for viewing the outputs of the applications and/or deployment pipeline(s) 210. For example, the GPUs 222 may be leveraged by the visualization services 220 to generate the visualizations. In addition, rendering effects, such as ray-tracing, may be implemented by the visualization services 220 to generate higher quality visualizations. The visualizations may include, without limitation, 2D image renderings, 3D volume renderings, 3D volume reconstruction, 2D tomographic slices, virtual reality displays, augmented reality displays, and/or the like. In some examples, virtualized environments may be used to generate a virtual interactive display or environment (e.g., a virtual environment) for interaction by users of the system (e.g., doctors, nurses, radiologists, etc.). In such examples, the visualization services 220 may include an internal visualizer, cinematics, and/or other rendering or image processing capabilities or functionality (e.g., ray tracing, rasterization, internal optics, etc.).

The hardware 122 may include GPUs 222, the AI system 224, the cloud 226, and/or any other hardware used for executing the training system 104 and/or the deployment system 106. The GPUs 222 (e.g., NVIDIA's TESLA and/or QUADRO GPUs) may include any number of GPUs that may be used for executing processing tasks of the compute services 216, the AI services 218, the visualization services 220, other services, and/or any of the features or functionality of the software 118. For example, with respect to the AI services 218, the GPUs 222 may be used to perform pre-processing on imaging data (or other data types used by machine learning models), post-processing on outputs of the machine learning models, and/or to perform the inferencing (e.g., to execute the machine learning models). The cloud 226, the AI system 224, and/or other components of the system 200 may use GPUs 222. For example, the cloud 226 may include a GPU-optimized platform for deep learning tasks. In addition, the AI system 224 may use GPUs, and the cloud 226—or at least a portion tasked with deep learning or inferencing—may be executed using one or more AI systems 224. As such, although the hardware 122 is illustrated as discrete components, this is not intended to be limiting, and any of the components of the hardware 122 may be combined with, or leveraged by, any of the other components of the hardware 122.

The AI system 224 may include a purpose-built computing system (e.g., a supercomputer or an HPC) configured for inferencing, deep learning, machine learning, and/or other artificial intelligence tasks. For example, the AI system 224 (e.g., NVIDIA's DGX) may include GPU-optimized software (e.g., a software stack) that may be executed using a plurality of GPUs 222, in addition to CPUs, RAM, storage, and/or other components, features, or functionality. In some embodiments, one or more AI systems 224 may be implemented in the cloud 226 (e.g., in a data center) for performing some or all of the AI-based processing tasks of the system 200.

The cloud 226 may include a GPU-accelerated infrastructure (e.g., NVIDIA's NGC) that may provide a GPU-optimized platform for executing processing tasks of the system 200. As described herein, in some examples, the cloud 226 may include an AI system(s) 224 for performing one or more of the AI-based tasks of the system 200 (e.g., as a hardware abstraction and scaling platform). The cloud 226 may integrate with the application orchestration system 228 leveraging multiple GPUs to enable seamless scaling and load balancing between and among the applications and services 120. The cloud 226 may tasked with executing at least some of the services 120 of the system 200, including compute services 216, AI services 218, and/or visualization services 220, as described herein. For example, the cloud 226 may perform small and large batch inference (e.g., executing NVIDIA's TENSOR RT), provide an accelerated parallel computing API and platform 230 (e.g., NVIDIA's CUDA), execute the application orchestration system 228 (e.g., KUBERNETES), provide a graphics rendering API and platform (e.g., for ray-tracing, 2D graphics, 3D graphics, and/or other rendering techniques to produce higher quality cinematics), and/or may provide other functionality for the system 200.

In some embodiments, in an effort to preserve patient confidentiality (e.g., where patient data or records are to be used off-premises), the cloud 226 may include a registry—such as a deep learning container registry. For example, the registry may store containers for instantiations of applications that may perform pre-processing, post-processing, or other processing tasks on patient data. As such, the cloud 226 may receive data that includes patient data as well as sensor data in containers, perform requested processing for just the sensor data in those containers, and then forward the resultant output and/or visualizations to the appropriate parties and/or devices (e.g., on-premises medical devices used for visualization or diagnoses), all without having to extract, store, or otherwise access the patient data. As a result, the confidentiality of the patient data is preserved in compliance with HIPAA and/or other data regulations.

Now referring to FIG. 3, FIG. 3 includes an example illustration of a deployment pipeline 210A for processing imaging data, in accordance with some embodiments of the present disclosure. As described herein, the system 200—and specifically the deployment system 106—may be used to customize, update, and/or integrate deployment pipeline (s) 210A into one or more production environments. The deployment pipeline 210A of FIG. 3 includes a non-limiting example of a deployment pipeline 210A that may be custom defined by a particular user (or team of users) at a facility (e.g., at a hospital, clinic, lab, research environment, etc.). For example, to define the deployment pipelines 210A for a CT scanner 302, the user may select—from a container registry, for example—one or more applications that perform specific functions or tasks with respect to the imaging data generated by the CT scanner 302. Instantiations of these applications may then be applied to the deployment pipeline 210A as containers that may leverage the services 120 and/or hardware 122 of the system 200. In addition, the deployment pipeline 210A may include additional processing tasks or applications that may be implemented to prepare the data for use by the applications (e.g., the DICOM adapter 202B and DICOM reader 306 may be used in the deployment pipeline 210A to prepare the data for use by CT reconstruction 308, organ segmentation 310, etc.). In addition, the deployment pipeline 210A may be customized or selected for consistent deployment, one time use, or for another frequency or interval. For example, a user may desire to have CT reconstruction 308 and organ segmentation 310 for several subjects over a specific interval, and thus may deploy the pipeline 210A for that period of time. As another example, a user may select, for each request from the system 200, the applications that the user wants to perform processing on that data for that request. As such, the deployment pipeline 210A may be adjusted at any interval and, because of the adaptability and scalability of the container structure within the system 200, this may be a seamless process.

The deployment pipeline 210A of FIG. 3 may include the CT scanner 302 generating imaging data of a patient or subject. The imaging data from the CT scanner 302 may be stored on a PACS server(s) 304 associated with the facility housing the CT scanner 302. The PACS server(s) 304 may include software and/or hardware components that may directly interface with imaging modalities (e.g., the CT scanner 302) at a facility. The DICOM adapter 202B may enable sending and receipt of DICOM objects using DICOM protocols. The DICOM adapter 202B may aid in the preparation or configuration of the DICOM data from the PACS server(s) 304 for use by the deployment pipeline 210A. Once the DICOM data is processed through the DICOM adapter 202B, the pipeline manager 212 may route the data through to the deployment pipeline 210A. For example, the DICOM reader 306 may extract the image files and any associated metadata from the DICOM data (e.g., raw sinogram data, as illustrated in visualization 316A). In some embodiments, the working files that are extracted may be stored in a cache for faster processing by other applications in the deployment pipeline 210A. Once the DICOM reader 306 has finished extracting and/or storing the data, a signal of completion may be communicated to the pipeline manager 212. The pipeline manager 212 may then initiate or call upon one or more other applications or containers in the deployment pipeline 210A.

For example, the CT reconstruction 308 application and/or container may be executed once the data (e.g., raw sinogram data) is available for processing by the CT reconstruction 308 application. CT reconstruction 308 may read the raw sinogram data from the cache, reconstruct an image file out of the raw sinogram data (e.g., as illustrated in visualization 316B), and store the resulting image file in the cache. At the completion of the reconstruction, the pipeline manager 212 may be signaled that the reconstruction task is complete. Once reconstruction is complete, and the reconstructed image file may be stored in the cache (or other storage device), the organ segmentation 310 application and/or container may be triggered by the pipeline manager 212. The organ segmentation 310 application and/or container may read the image file from the cache, normalize or convert the image file to format suitable for inference (e.g., convert the image file to an input resolution of a machine learning model), and run inference against the normalized image. To run inference on the normalized image, the organ segmentation 310 application and/or container may rely on the services 120, and the pipeline manager 212 and/or application orchestration system 228 may facilitate the use of the services 120 by the organ segmentation 310 application and/or container. For example, the organ segmentation 310 application and/or container may leverage the AI services 218 to perform inference on the normalized image, and the AI services 218 may leverage the hardware 122 (e.g., the AI system 224) to execute the AI services 218. The result of the inference may be a mask file (e.g., as illustrated in visualization 316C) that may be stored in the cache (or other storage device).

Once the applications that process the DICOM data and/or data extracted from the DICOM data have completed processing, a signal may be generated for the pipeline manager 212. The pipeline manager 212 may then execute the DICOM writer 312 to read the results from the cache (or other storage device), package the results into a DICOM format (e.g., as DICOM output 314) for use by users at the facility who generated the request. The DICOM output 314 may then be transmitted to the DICOM adapter 202B to prepare the DICOM output 314 for storage on the PACS server(s) 304 (e.g., for viewing by a DICOM viewer at the facility). As such, in response to the request for reconstruction and segmentation, the visualizations 316B and 316C may be generated and available to the user for diagnoses, research, and/or for other purposes.

Although illustrated as consecutive application in the deployment pipeline 210A, the CT reconstruction 308 and organ segmentation 310 applications may be processed in parallel. For example, where the applications do not have dependencies on one another, and the data is available for each application (e.g., after the DICOM reader 306 extracts the data), the applications may be executed at the same time, substantially at the same time, or with some overlap. As described herein, where two or more applications require similar services 120, a scheduler of the system 200 may be used to load balance and distribute compute or processing resources between and among the various applications. In addition, in some embodiments, the parallel computing platform 230 may be used to perform parallel processing for the applications to decrease run-time of the deployment pipeline 210A to provide real-time results.

Figure 4A:
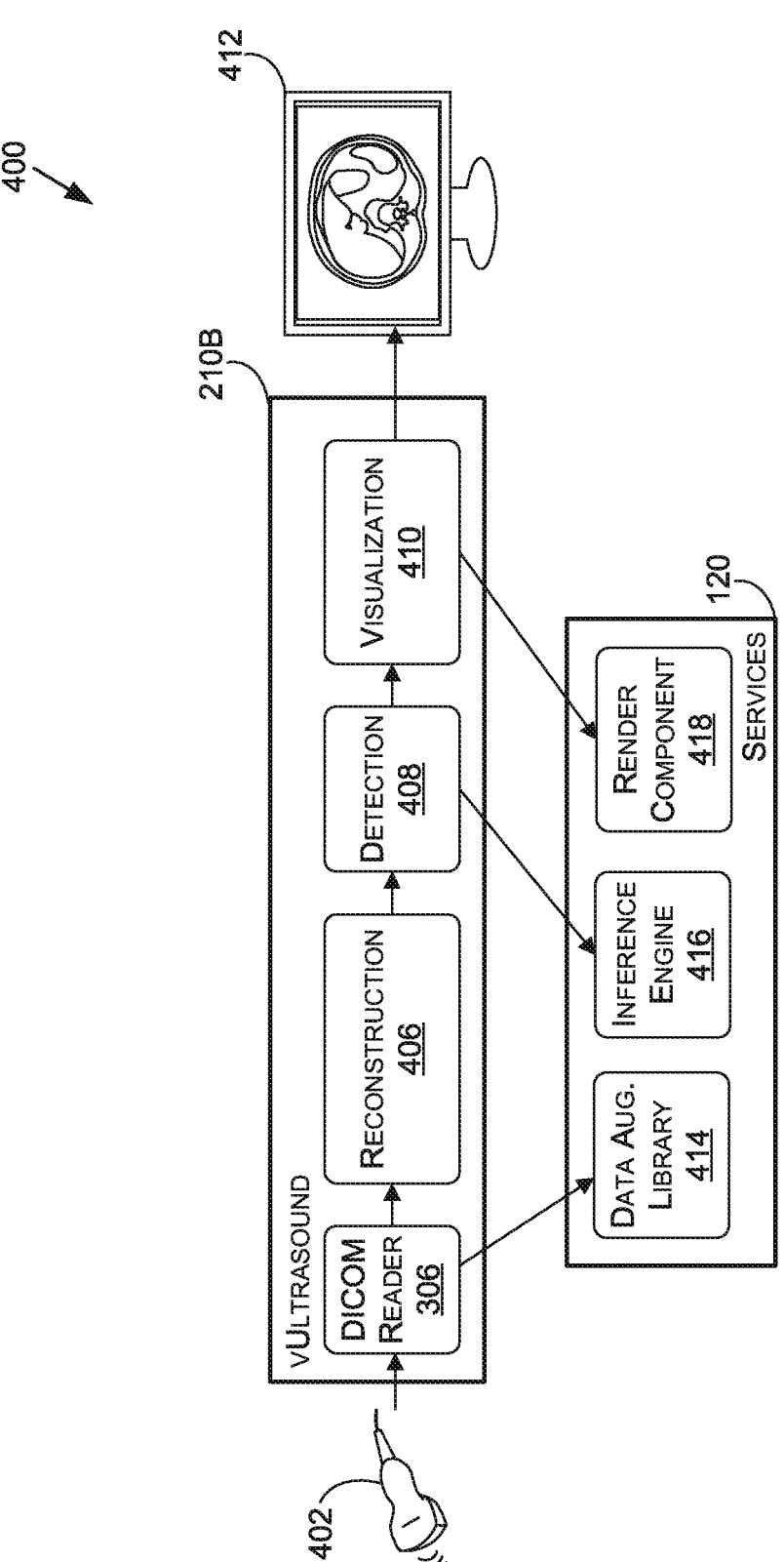
FIG. 4A includes an example data flow diagram of a virtual instrument supporting an ultrasound device, in accordance with some embodiments of the present disclosure.
Figure 4B:
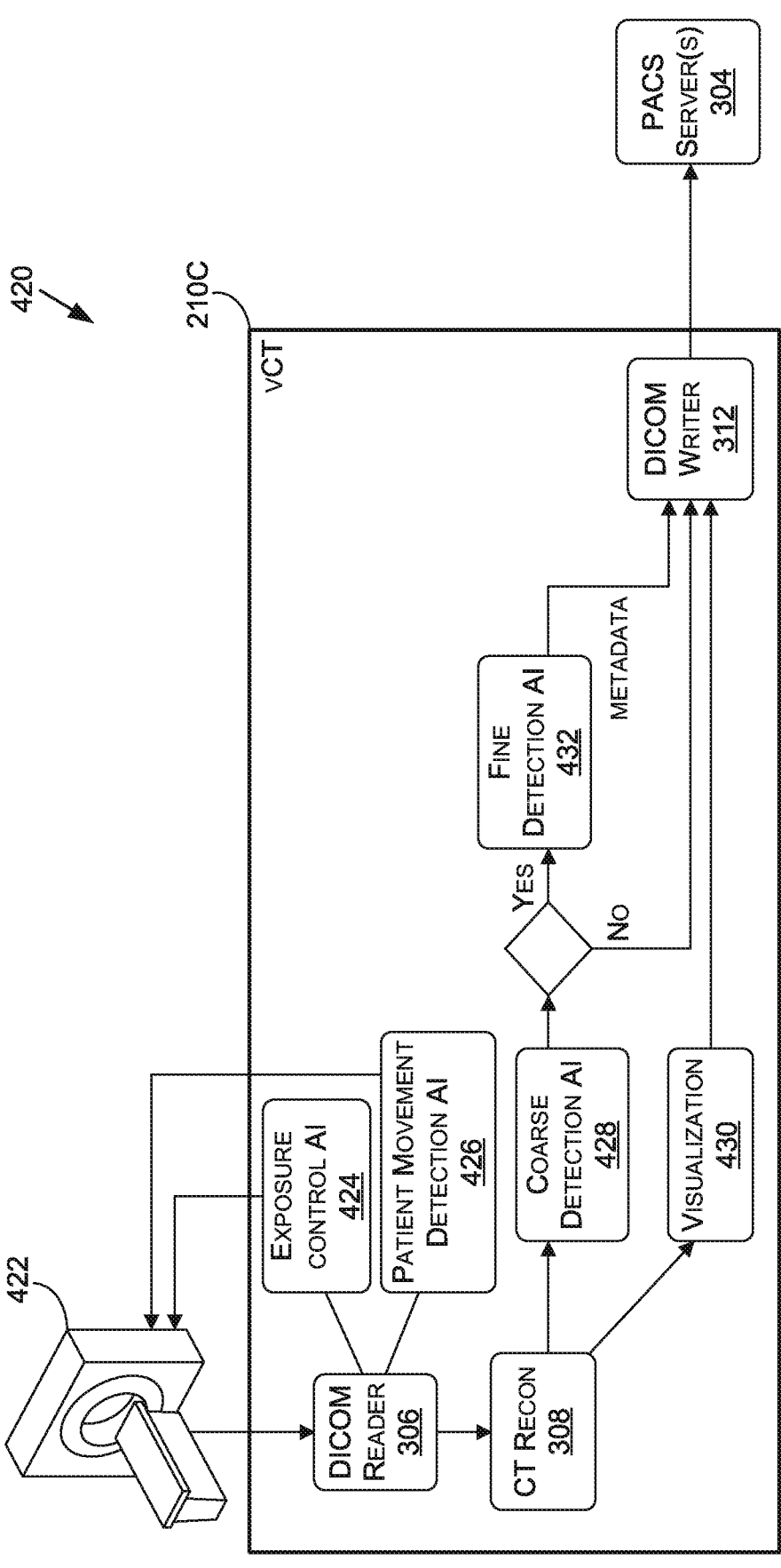
FIG. 4B includes an example data flow diagram of a virtual instrument supporting an CT scanner, in accordance with some embodiments of the present disclosure.

In some embodiments, and with reference to FIGS. 4A-4B, the deployment system 106 may be implemented as one or more virtual instruments to perform different functionalities—such as image processing, segmentation, enhancement, AI, visualization, and inferencing—with imaging devices (e.g., CT scanners, X-ray machines, MRI machines, etc.), sequencing devices, genomics devices, and/ or other device types. The system 200 may allow for the creation and provision of virtual instruments that may include a software-defined deployment pipeline 210 that may receive raw/unprocessed input data generated by a device(s) and output processed/reconstructed data. The deployment pipelines 210 (e.g., 210A and 210B) that represent the virtual instruments may implement intelligence into the pipeline, such as by leveraging machine learning models, to provide containerized inference support to the system. As such, the virtual instruments may execute any number of containers each including instantiations of applications while leveraging services 120 and/or hardware 122 of the system to facilitate execution. In some examples, such as where real-time processing is desired, the deployment pipelines 210 representing the virtual instruments may be static (e.g., the containers and/or applications may be set), while in other examples, container and/or applications for the virtual instruments may be selected (e.g., on a per-request basis) from a pool of applications or resources (e.g., within a container registry).

As such, the system 200 may be instantiated or executed as one or more virtual instruments on-premise at a facility in, for example, a computing system deployed next to or otherwise in communication with a radiology machine, an imaging device, and/or another device type at the facility. In some embodiments, however, the on-premise installation may be instantiated or executed within the computing system of the device itself (e.g., a computing system integral to the imaging device), in a local datacenter (e.g., a datacenter on-premise), and/or in a cloud-environment (e.g., in the cloud 226). The deployment system 106, operating as a virtual instrument, may be instantiated by a supercomputer or other HPC system in some examples. On-premise installation may allow for high-bandwidth uses (via, for example, higher throughput local communication interfaces, such as RF over Ethernet) for real-time processing. Real-time or near real-time processing may be particularly useful where a virtual instrument supports an ultrasound device or other imaging modality where immediate visualizations are expected or required for accurate diagnoses and analyses. A cloud-computing architecture may be capable of dynamic bursting to a cloud computing service provider, or other compute cluster, when local demand exceeds on-premise capacity or capability. Additionally, the cloud architecture, when implemented, may be tuned for training neural networks or other machine learning models, as described herein with respect to the training system 104. As such, with training pipelines in place, machine learning models may be continuously learn and improve as they process additional data from the devices they support. In such examples, the virtual instruments may be continually improved using additional data, new data, existing machine learning models, and/or new or updated machine learning models.

As described herein, the computing system according to one or more embodiments may include some or all of the hardware 122 described herein, and the hardware 122 may be distributed in any of a number of ways including within the device, as part of a computing device coupled to and located proximate the device, in a local datacenter at the facility, and/or in the cloud 226. In any example, because the deployment system 106 and the associated applications or containers are created in software (e.g., as discrete containerized instantiations of applications), the behavior, operation, and configuration of the virtual instruments, as well as the outputs generated by the virtual instruments, may be modified or customized as desired, without having to change or alter the raw output of the device that the virtual instrument supports.

FIG. 4A includes an example data flow diagram of a virtual instrument supporting an ultrasound device, in accordance with some embodiments of the present disclosure. As illustrated, the deployment pipeline 210B may leverage one or more of the services 120 of the system 200. As described herein, the deployment pipeline 210B and the services 120 may leverage the hardware 122 of the system either locally or in the cloud 226. In addition, although not illustrated, the process 400 may be facilitated by the pipeline manager 212, the application orchestration system 228, and/or the parallel computing platform 230.

The process 400 may include receipt of imaging data from an ultrasound device 402. The imaging data may be stored on PACS server(s) in a DICOM format (or other format, such as RIS, CIS, REST compliant, RPC, raw, etc.), and may be received by the system 200 for processing through the deployment pipeline 210 selected or customized as the virtual instrument (e.g., the virtual ultrasound) for the ultrasound device 402. In some examples, the imaging data may be received directly from the imaging device (e.g., the ultrasound device 402) and processed by the virtual instrument. In other examples, a transducer or other signal converter communicatively coupled between the imaging device and the virtual instrument may convert the signal data generated by the imaging device to image data that may be processed by the virtual instrument. In either example, the raw data and/or the image data may be applied to the DICOM reader 306 to extract the data for use by the applications or containers of the deployment pipeline 210B. The DICOM reader 306 may leverage the data augmentation library 414 (e.g., NVIDIA's DALI) as a service 120 (e.g., as one of the compute service(s) 216) for extracting, resizing, rescaling, and/or otherwise preparing the data for use by the applications or containers.

Once the data is prepared, a reconstruction 406 application and/or container may be executed to reconstruct the data from the ultrasound device 402 into an image file. After reconstruction 406, or at the same time as reconstruction 406, a detection 408 application and/or container may be executed for anomaly detection, object detection, feature detection, and/or other detection tasks related to the data. For example, the image file generated during the reconstruction 406 may be used during detection 408 to identify the anomalies, objects, features, etc. The detection 408 application may leverage an inference engine 416 (e.g., as one of the AI service(s) 218) to perform inference on the data to generate the detections. For example, one or more machine learning models (e.g., from the training system 104) may be executed or called by the detection 408 application.

Once the reconstruction 406 and/or the detection 408 is/are complete, the data output from these application and/or containers may be used to generate visualizations 410, such as visualization 412 (e.g., a grayscale output) displayed on a workstation or display terminal. The visualization may allow a technician or other user to visualize the results of the deployment pipeline 210B with respect to the ultrasound device 402. The visualization 410 may be executed by leveraging a render component 418 of the system 200 (e.g., one of the visualization service(s) 220). For example, the render component 418 may execute a 2D, OpenGL, or ray-tracing service to generate the visualization 412.

FIG. 4B includes an example data flow diagram of a virtual instrument supporting a CT scanner, in accordance with some embodiments of the present disclosure. Although not illustrated, the deployment pipeline 210C may leverage one or more of the services 120 of the system 200. As described herein, the deployment pipeline 210C and the services 120 may leverage the hardware 122 of the system either locally or in the cloud 226. In addition, although not illustrated, the process 420 may be facilitated by the pipeline manager 212, the application orchestration system 228, and/or the parallel computing platform 230.

The process 420 may include the CT scanner 422 generating raw data that may be received by the DICOM reader 306 (e.g., directly, via a PACS server 304, after processing, etc.). A Virtual CT (instantiated by the deployment pipeline 210C) may include a first, real-time pipeline for monitoring the patient (e.g., patient movement detection AI 426) and/or for adjusting or optimizing the exposure of the CT scanner 422 (e.g., using the exposure control AI 424). One or more of the applications (e.g., 424 and 426) may leverage a service 120, such as the AI service(s) 218. The outputs of the exposure control AI 424 application (or container) and/or the patient movement detection AI 426 application (or container) may be used as feedback to the CT scanner 422 and/or the technician for adjusting the exposure (or other settings of the CT scanner 422) and/or informing the patient to move less.

Another pipeline of the deployment pipeline 210C may include a non-real-time pipeline for analyzing data generated by the CT scanner 422. The second pipeline may include the CT reconstruction 308 application and/or container, a coarse detection AI 428 application and/or container, a fine detection AI 432 application and/or container (e.g., where certain results are detected by the coarse detection AI 428), a visualization 430 application and/or container, and a DICOM writer 312 (and/or other data type writer, such as RIS, CIS, REST compliant, RPC, raw, etc.) application and/or container. As such, the raw data generated by the CT scanner 422 may be passed through the pipelines of the deployment pipeline 210C (instantiated as a virtual CT instrument) to generate results. The results from the DICOM writer 312 may be transmitted for display and/or may be stored on the PACS server(s) 304 for later retrieval, analysis, or display by a technician, practitioner, or other user.

Now referring to FIG. 5, each block of method 500, described herein, comprises a computing process that may be performed using any combination of hardware, firmware, and/or software. For instance, various functions may be carried out by a processor executing instructions stored in memory. The method 500 may also be embodied as computer-usable instructions stored on computer storage media. The method 500 may be provided by a standalone application, a service or hosted service (standalone or in combination with another hosted service), or a plug-in to another product, to name a few. In addition, method 500 is described, by way of example, with respect to the system of FIG. 2. However, this method may additionally or alternatively be executed by any one system, or any combination of systems, including, but not limited to, those described herein.

FIG. 5 is a flow diagram showing a method 500 for deploying an image inferencing pipeline in accordance with some embodiments of the present disclosure. The method 500, at block B502, includes receiving a selection of applications to perform processing requests. For example, a user (e.g., practitioner, clinician, scientist, etc.) may select one or more applications for inclusion in a deployment pipeline 210 for processing any of a variety of different types of data (e.g., DICOM data, RIS data, CIS data, RPC data, data substantially compliant with a REST interface, data substantially compliant with a file-based interface, and/or raw data (e.g., raw image data)).

The method 500, at block B504, includes instantiating a deployment pipeline to perform the processing requests, the deployment pipeline including container(s) comprising executable instantiations of the applications from the selection. For example, the deployment system 106 may instantiate the deployment pipeline 210 for the applications. In such an example, image files corresponding to the applications may be used to generate discrete, containerized, instantiations of the applications.

The method 500, at block B506, includes, for at least one containers(s), determining services to perform one or more operations for an executable instantiation of an application comprised by the container. For example, to deploy the deployment pipeline 210, one or more services 120 may be used to perform at least some of the processing for the instantiations of the applications in one or more of the containers. In such an example, AI services 218 may be used to execute machine learning models corresponding to applications.

The method 500, at block B508, includes receiving a processing request corresponding to data generated by a device. For example, a processing request (or inference request) may be received for processing data from an imaging device, a radiology device, a gene sequencing device, and/or another device type. The request may be received automatically from a system executing the device (e.g., the deployment pipeline 210 may be static, or set, with respect to the device, such as where the deployment pipeline 210 corresponds to a virtual instrument). In other examples, the processing request may be received in response to a selection by a user.

The method 500, at block B510, includes receiving the data. For example, the data corresponding to the processing request may be received by the system 200.

The method 500, at block B512, includes processing the data according to the deployment pipeline and using the service(s) to generate processed data. For example, the deployment pipeline 210 may be used, in combination with one or more of the services 120 and/or the hardware 122, to process the data.

Now referring to FIG. 6A, FIG. 6A illustrates a data flow diagram for a process 600 to train, retrain, or update a machine learning model, in accordance with some embodiments of the present disclosure. The process 600 may be executed using, as a non-limiting example, the system 200 of FIG. 2. As such, the process 600 may leverage the services 120 and/or the hardware 122 of the system 200, as described herein. In addition, the refined models 612 generated by the process 600 may be executed by the deployment system 106 for one or more containerized applications in the deployment pipelines 210.

As described herein, model training 114 may include retraining or updating an initial model 604 (e.g., a pre-trained model) using new training data (e.g., new input data, such as the customer dataset 606, and/or new ground truth data associated with the input data). To retrain, or update, the initial model 604, the output or loss layer(s) of the initial model 604 may be reset, or deleted, and/or replaced with an updated or new output or loss layer(s). As such, the initial model 604 may have previously fine-tuned parameters (e.g., weights and/or biases) that remain from prior training, so training or retraining 114 may not take as long or require as much processing as training a model from scratch. During model training 114, by having reset or replaced the output or loss layer(s) of the initial model 604, the parameters may be updated and re-tuned for a new data set based on loss calculations associated with the accuracy of the output or loss layer(s) at generating predictions on the new, customer dataset 606 (e.g., the image data 108 of FIG. 1).

The pre-trained models 206 may be stored in a data store, or registry (e.g., the model registry 124 of FIG. 1). In some embodiments, the pre-trained models 206 may have been trained, at least in part, at one or more facilities other than the facility executing the process 600. For example, to protect the privacy and rights of patients, subjects, or clients of different facilities, the pre-trained models 206 may have been trained, on-premise, using customer or patient data generated on-premise. In some examples, the pre-trained models 206 may be trained using the cloud 226 and/or other hardware 122, but the confidential, privacy protected patient data may not be transferred to, used by, or accessible to any components of the cloud 226 (or other off premise hardware). As such, where a pre-trained model 206 is trained at using patient data from more than one facility, the pre-trained model 206 may have been individually trained for each facility prior to being trained on patient or customer data from another facility. In other embodiments, such as where the customer or patient data has been released of privacy concerns (e.g., by waiver, for experimental use, etc.), or where the customer or patient data is included in a public data set, the customer or patient data from any number of facilities may be used to train the pre-trained model 206 on-premise and/or off premise, such as in a datacenter or other cloud computing infrastructure.

When selecting the applications for use in the deployment pipelines 210, the user may also select machine learning models to be used for specific applications. However, in some examples, the user may not have a model for use, so the user may select a pre-trained model 206 to use with an application. Once selected, however, the pre-trained model 206 may not be optimized for generating accurate results on the customer dataset 606 of the facility of the user (e.g., based on patient diversity, demographics, types of medical imaging devices used, etc.). In such examples, prior to deploying the pre-trained model 206 into the deployment pipeline 210 for use with an application(s), the pre-trained model 206 may be updated, retrained, and/or fine-tuned for use at the respective facility.

The user may select the pre-trained model 206 that is to be updated, retrained, and/or fine-tuned, and the pre-trained model 206 may be referred to as the initial model 604 for the training system 104 within the process 600. The customer dataset 606 (e.g., imaging data, genomics data, sequencing data, or other data types generated by devices at the facility) may be used to perform model training 114 (which may include, without limitation, transfer learning) on the initial model 604 to generate the refined model 612. Ground truth data corresponding to the customer dataset 606 may be generated by the training system 104. In some examples, the ground truth data may be generated, at least in part, by clinicians, scientists, doctors, practitioners, and/or the like at the facility (e.g., as the labeled clinic data 112 of FIG. 1).

AI-assisted annotation 110 may be used in some examples to generate the ground truth data. For example, AI-assisted annotation 110 (e.g., implemented using an AI-assisted annotation SDK) may leverage machine learning models (e.g., neural networks) to generate suggested or predicted ground truth data for the customer dataset. A user 610 may use annotation tools within a user interface (a graphical user interface (GUI)) on computing device 608.

According to embodiments, a user 610 may interact with the GUI via computing device 608 to edit or fine-tune the (auto)annotations. For example, a polygon editing feature may be used to move vertices of the polygon to more accurate or fine-tuned locations. With reference to FIG. 6B, a screenshot of AI-assisted annotation GUI 614 is illustrated. The screenshot of the GUI 614 may include an auto-annotated result generated during AI-assisted annotation 110. A 2D slice 620 of a plurality of organs may be populated within the GUI 614, and an organ or abnormality may be annotated with an annotation 622. The annotation 622 may include a plurality of vertices of a polygon that may be movable by the user 610. For example, the user 610 may add additional vertices, remove vertices, and/or move vertices around within the 2D slice 620. In addition, the user 610 may use one or more tools 618 for adjusting the annotation 622. Prior to submitting the data for AI-assisted annotation 110, the user 610 may select a model, a number of points or vertices, and/or other information for generating the annotation 622 within an annotation window 624 of the GUI 614. In addition, the user 610 may apply study labels 626, image labels 628 (e.g., classifications), notes 630, and/or or perform other tasks within the GUI 614 for generating, editing, and/or associating metadata with the annotation 622 and/or the 2D slice 620.

Once the customer dataset 606 has associated ground truth data, the ground truth data (e.g., from AI-assisted annotation, manual labeling, etc.) may be used by during model training 114 to generate the refined model 612. For example, the customer dataset 606 may be applied to the initial model 604 any number of times, and the ground truth data may be used to update the parameters of the initial model 604 until an acceptable level of accuracy is attained for the refined model 612. Once the refined model 612 is generated, the refined model 612 may be deployed within one or more deployment pipelines 210 at a facility for performing one or more processing tasks with respect to medical imaging data.

In some examples, the refined model 612 may be uploaded to the pre-trained models 206 in the model registry 124 to be selected by another facility. This process may be completed at any number of facilities such that the refined model 612 may be further refined on new datasets any number of times to generate a more universal model.

With reference to FIG. 6C, FIG. 6C is an example illustration of a client-server architecture 632 to enhance annotation tools with pre-trained annotation models, in accordance with some embodiments of the present disclosure. In an example embodiment, AI-assisted annotation tools 636 may be instantiated based on a client-server architecture 632. The annotation tools 636 in imaging applications may aid radiologists, for example, identify organs and abnormalities. The imaging applications may include software tools that help the user 610 to identify, as a non-limiting example, a few extreme points on a particular organ of interest in raw images 634 (e.g., in a 3D MRI or CT scan) and receive auto-annotated results for all the 2D slices of the particular organ. The results may be stored in a data store as training data 638 and used as (for example and without limitation) ground truth data for training. In such an example, when the computing device 608 sends the extreme points for AI-assisted annotation 110, a deep learning model, for example, may receive this data as input and return the inference results of the segmented organ or abnormality. For example, pre-instantiated annotation tools, such as AI-Assisted Annotation Tool 636B in FIG. 6C, may be enhanced by making API calls (e.g., API Call 644) to a server, such as an Annotation Assistant Server 640 that may include a set of pre-trained models 642 stored in an annotation model registry, for example. The annotation model registry may store the pre-trained models 642 (e.g., machine learning models, such as deep learning models) that are pre-trained to perform AI-assisted annotation on a particular organ or abnormality. These models may be further updated by using training pipelines 204. As a result, pre-installed annotation tools may be improved over time as new labeled clinic data 112 is added.

Now referring to FIG. 7, each block of method 700, described herein, comprises a computing process that may be performed using any combination of hardware, firmware, and/or software. For instance, various functions may be carried out by a processor executing instructions stored in memory. The method 700 may also be embodied as computer-usable instructions stored on computer storage media. The method 700 may be provided by a standalone application, a service or hosted service (standalone or in combination with another hosted service), or a plug-in to another product, to name a few. In addition, method 700 is described, by way of example, with respect to the process 600 of FIG. 6A. However, this method may additionally or alternatively be executed by any one system, or any combination of systems, including, but not limited to, those described herein.

FIG. 7 is a flow diagram showing a method 700 to train a machine learning model for deployment in an image inferencing pipeline, in accordance with some embodiments of the present disclosure. The method 700, at block B702, includes receiving an input corresponding to a selection of a neural network from a model registry. For example, an initial model 604 may be selected from pre-trained models 206 of a model registry 124 (FIG. 1).

The method 700, at block B704, includes receiving the neural network. For example, data corresponding to the neural network may be received and/or data indicating a location of the neural network may be received.

The method 700, at block B706, includes receiving data generated by a device(s). For example, DICOM, RIS, CIS, REST compliant, RPC, raw, and/or other data types, such as from the customer dataset 606, may be received, where the data may be generated by any type of device(s), including but not limited to imaging devices, radiology devices, gene sequencing devices, genomics devices, and/or the like.

The method 700, at block B708, includes generating ground truth data corresponding to the data. For example, the ground truth data may be generated as labeled clinic data 112 (FIG. 1), AI-assisted annotation 110 data, or a combination thereof.

The method 700, at block B710, includes retraining the neural network using the data and the ground truth data to generate an updated neural network. For example, model training 114 may be used to retrain, update, and/or fine-tune the initial model 604 to generate the refined model 612.

The method 700, at block B712, includes deploying the updated neural network for use with a containerized instantiation of an application. For example, the refined model 612 may be deployed by the system 200 and leveraged (e.g., as a service 120) during processing of a containerized instantiation of an application.

Example Computing Device

Figure 8:
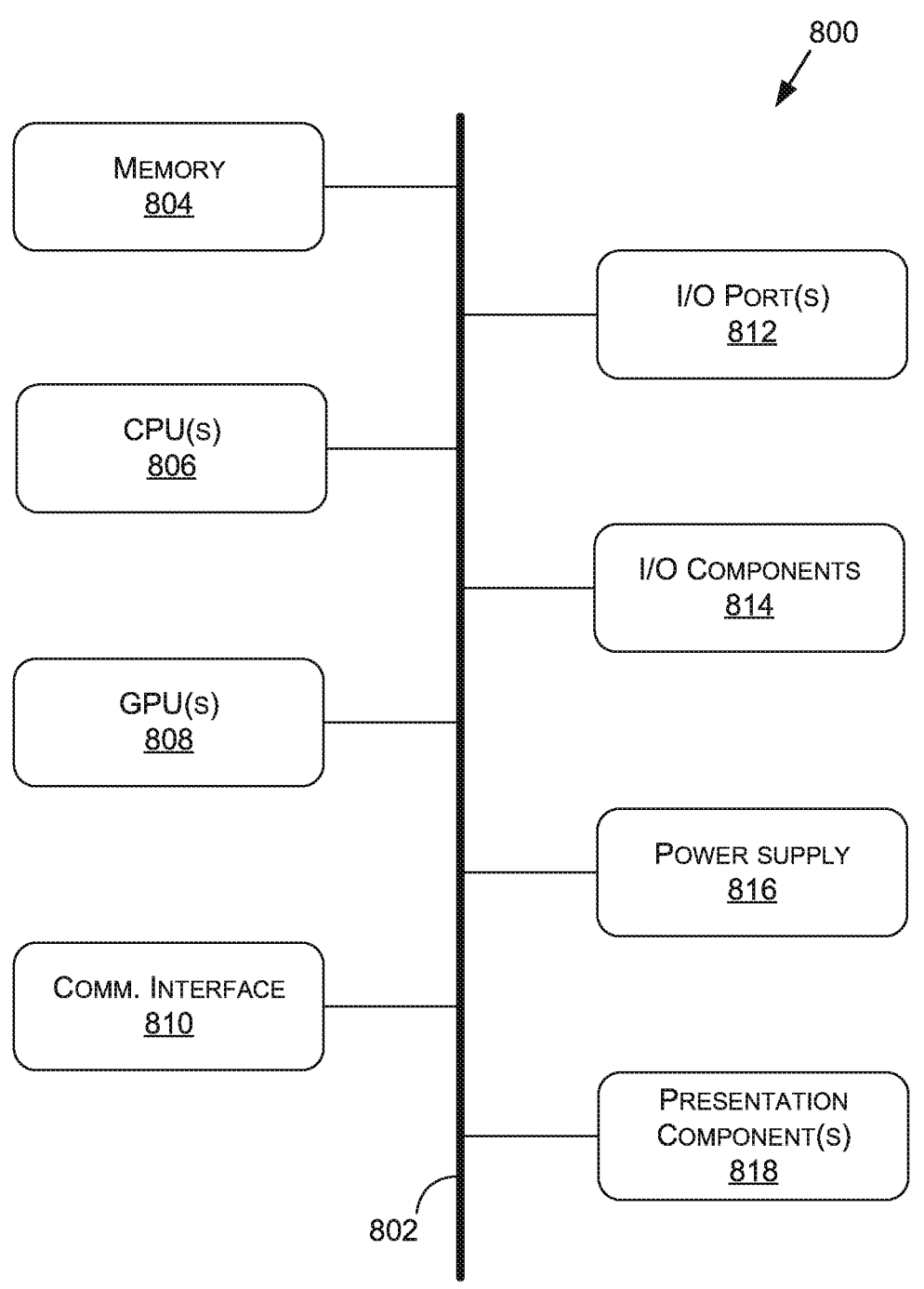
FIG. 8 is a block diagram of an example computing device suitable for use in implementing some embodiments of the present disclosure.

FIG. 8 is a block diagram of an example computing device 800 suitable for use in implementing some embodiments of the present disclosure. Computing device 800 may include a bus 802 that directly or indirectly couples the following devices: memory 804, one or more central processing units (CPUs) 806, one or more graphics processing units (GPUs) 808, a communication interface 810, input/output (I/O) ports 812, input/output components 814, a power supply 816, and one or more presentation components 818 (e.g., display(s)).

Although the various blocks of FIG. 8 are shown as connected via the bus 802 with lines, this is not intended to be limiting and is for clarity only. For example, in some embodiments, a presentation component 818, such as a display device, may be considered an I/O component 814 (e.g., if the display is a touch screen). As another example, the CPUs 806 and/or GPUs 808 may include memory (e.g., the memory 804 may be representative of a storage device in addition to the memory of the GPUs 808, the CPUs 806, and/or other components). In other words, the computing device of FIG. 8 is merely illustrative. Distinction is not made between such categories as "workstation," "server," "laptop," "desktop," "tablet," "client device," "mobile device," "handheld device," "game console," "electronic control unit (ECU)," "virtual reality system," and/or other device or system types, as all are contemplated within the scope of the computing device of FIG. 8.

The bus 802 may represent one or more busses, such as an address bus, a data bus, a control bus, or a combination thereof. The bus 802 may include one or more bus types, such as an industry standard architecture (ISA) bus, an extended industry standard architecture (EISA) bus, a video electronics standards association (VESA) bus, a peripheral component interconnect (PCI) bus, a peripheral component interconnect express (PCIe) bus, and/or another type of bus.

The memory 804 may include any of a variety of computer-readable media. The computer-readable media may be any available media that may be accessed by the computing device 800. The computer-readable media may include both volatile and nonvolatile media, and removable and non-removable media. By way of example, and not limitation, the computer-readable media may comprise computer-storage media and communication media.

The computer-storage media may include both volatile and nonvolatile media and/or removable and non-removable media implemented in any method or technology for storage of information such as computer-readable instructions, data structures, program modules, and/or other data types. For example, the memory 804 may store computer-readable instructions (e.g., that represent a program(s) and/or a program element(s), such as an operating system. Computer-storage media may include, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which may be used to store the desired information and which may be accessed by computing device 800. As used herein, computer storage media does not comprise signals per se.

The communication media may embody computer-readable instructions, data structures, program modules, and/or other data types in a modulated data signal such as a carrier wave or other transport mechanism and includes any information delivery media. The term "modulated data signal" may refer to a signal that has one or more of its characteristics set or changed in such a manner as to encode information in the signal. By way of example, and not limitation, the communication media may include wired media such as a wired network or direct-wired connection, and wireless media such as acoustic, RF, infrared and other wireless media. Combinations of any of the above should also be included within the scope of computer-readable media.

The CPU(s) 806 may be configured to execute the computer-readable instructions to control one or more components of the computing device 800 to perform one or more of the methods and/or processes described herein. The CPU(s) 806 may each include one or more cores (e.g., one, two, four, eight, twenty-eight, seventy-two, etc.) that are capable of handling a multitude of software threads simultaneously. The CPU(s) 806 may include any type of processor, and may include different types of processors depending on the type of computing device 800 implemented (e.g., processors with fewer cores for mobile devices and processors with more cores for servers). For example, depending on the type of computing device 800, the processor may be an ARM processor implemented using Reduced Instruction Set Computing (RISC) or an x86 processor implemented using Complex Instruction Set Computing (CISC). The computing device 800 may include one or more CPUs 806 in addition to one or more microprocessors or supplementary co-processors, such as math co-processors.

The GPU(s) 808 may be used by the computing device 800 to render graphics (e.g., 3D graphics). The GPU(s) 808 may include hundreds or thousands of cores that are capable of handling hundreds or thousands of software threads simultaneously. The GPU(s) 808 may generate pixel data for output images in response to rendering commands (e.g., rendering commands from the CPU(s) 806 received via a host interface). The GPU(s) 808 may include graphics memory, such as display memory, for storing pixel data. The display memory may be included as part of the memory 804. The GPU(s) 708 may include two or more GPUs operating in parallel (e.g., via a link). When combined together, each GPU 808 may generate pixel data for different portions of an output image or for different output images (e.g., a first GPU for a first image and a second GPU for a second image). Each GPU may include its own memory, or may share memory with other GPUs.

In examples where the computing device 800 does not include the GPU(s) 808, the CPU(s) 806 may be used to render graphics.

The communication interface 810 may include one or more receivers, transmitters, and/or transceivers that enable the computing device 700 to communicate with other computing devices via an electronic communication network, included wired and/or wireless communications. The communication interface 810 may include components and functionality to enable communication over any of a number of different networks, such as wireless networks (e.g., Wi-Fi, Z-Wave, Bluetooth, Bluetooth LE, ZigBee, etc.), wired networks (e.g., communicating over Ethernet), low-power wide-area networks (e.g., LoRaWAN, SigFox, etc.), and/or the Internet.

The I/O ports 812 may enable the computing device 800 to be logically coupled to other devices including the I/O components 814, the presentation component(s) 818, and/or other components, some of which may be built in to (e.g., integrated in) the computing device 800. Illustrative I/O components 814 include a microphone, mouse, keyboard, joystick, game pad, game controller, satellite dish, scanner, printer, wireless device, etc. The I/O components 814 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing device 800. The computing device 800 may be include depth cameras, such as stereoscopic camera systems, infrared camera systems, RGB camera systems, touchscreen technology, and combinations of these, for gesture detection and recognition. Additionally, the computing device 800 may include accelerometers or gyroscopes (e.g., as part of an inertia measurement unit (IMU)) that enable detection of motion. In some examples, the output of the accelerometers or gyroscopes may be used by the computing device 800 to render immersive augmented reality or virtual reality.

The power supply 816 may include a hard-wired power supply, a battery power supply, or a combination thereof. The power supply 816 may provide power to the computing device 800 to enable the components of the computing device 800 to operate.

The presentation component(s) 818 may include a display (e.g., a monitor, a touch screen, a television screen, a heads-up-display (HUD), other display types, or a combination thereof), speakers, and/or other presentation components. The presentation component(s) 818 may receive data from other components (e.g., the GPU(s) 808, the CPU(s) 806, etc.), and output the data (e.g., as an image, video, sound, etc.).

The disclosure may be described in the general context of computer code or machine-useable instructions, including computer-executable instructions such as program modules, being executed by a computer or other machine, such as a personal data assistant or other handheld device. Generally, program modules including routines, programs, objects, components, data structures, etc., refer to code that perform particular tasks or implement particular abstract data types. The disclosure may be practiced in a variety of system configurations, including handheld devices, consumer electronics, general-purpose computers, more specialty computing devices, etc. The disclosure may also be practiced in distributed computing environments where tasks are performed by remote-processing devices that are linked through a communications network.

As used herein, a recitation of "and/or" with respect to two or more elements should be interpreted to mean only one element, or a combination of elements. For example, "element A, element B, and/or element C" may include only element A, only element B, only element C, element A and element B, element A and element C, element B and element C, or elements A, B, and C. In addition, "at least one of element A or element B" may include at least one of element A, at least one of element B, or at least one of element A and at least one of element B. Further, "at least one of element A and element B" may include at least one of element A, at least one of element B, or at least one of element A and at least one of element B.

The subject matter of the present disclosure is described with specificity herein to meet statutory requirements. However, the description itself is not intended to limit the scope of this disclosure. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

What is claimed is:

1. A web-based service, comprising:
   a user interface to allow one or more users of the web-based service to select one or more neural network data processing programs from a container registry and one or more selected neural networks from a model registry, wherein the model registry comprises a plurality of neural networks trained on data in different locations to perform different inferencing tasks; and
   cause the web-based service to use the selected one or more neural networks to use information generated by the one or more selected neural network data processing programs to implement a sequence of processing operations, wherein the sequence of processing operations include a combination of:
   inferencing using the one or more selected neural networks,
   generating a visualization based, at least in part, on data generated from the inferencing by the one or more selected neural networks, and
   transmitting display data corresponding to the visualization to a computing system for display by the computing system, wherein the computing system comprises an augmented reality (AR) system or a virtual reality (VR) system.

2. The web-based service of claim 1, wherein the web-based service receives data from an on-premise computing system, prepares the data for the one or more selected neural network data processing programs, applies the data to each of the one or more selected neural network data processing programs, and prepares the data generated from the one or more selected neural network data processing programs for use by the one or more selected neural networks at the on-premise computing system.

3. The web-based service of claim 2, wherein the data received from the on-premise computing system is to be processed before the data is to be used by the one or more selected neural network data processing programs to generate output to train the one or more selected neural networks.

4. The web-based service of claim 3, wherein the on-premise computing system is a medical imaging device.

5. The web-based service of claim 4, wherein the data received from the medical imaging device comprises raw medical image data.

6. The web-based service of claim 5, further comprising:
   processing the raw medical image data, using the one or more selected neural network data processing programs, to generate an image.

7. The web-based service of claim 1, further comprising:
   implementing a deployment pipeline within a computing system to include the one or more selected neural networks and the one or more selected neural network data processing programs.

8. The web-based service of claim 7, wherein at least one of the one or more selected neural network data processing programs is hosted remotely from the computing system.

9. The web-based service of claim 1, wherein the one or more selected neural networks includes performing operations comprising using at least one of: a computer vision algorithm, an object detection algorithm, an image reconstruction algorithm, and a gene sequencing algorithm.

10. The web-based service of claim 1, further comprising:
    performing one or more operations on data generated by the one or more selected neural networks before transmission to the one or more users.

11. The web-based service of claim 1, wherein data to be used by the one or more selected neural network data processing programs include at least one of: digital imaging and communications in medicine (DICOM) data, remote procedure call (RPC) data, data substantially compliant with a REST interface, data substantially compliant with a file-based interface, raw data, and radiological information system (RIS) data.

12. A system, comprising one or more processors comprising:

circuitry to implement a sequence of processing operations using information generated by one or more selected neural networks performing one or more selected neural network data processing programs, and to execute a web-based service, the web-based service comprising:

a user interface to allow one or more users of the web-based service to select the one or more selected neural network data processing programs from a container registry and the one or more selected neural networks from a model registry, wherein the model registry comprises a plurality of neural networks trained on data in different locations to perform different inferencing tasks and wherein the sequence of processing operations include a combination of:

inferencing using the one or more selected neural networks, generating a visualization based, at least in part, on data generated from the inferencing by the one or more selected neural networks, and transmitting display data corresponding to the visualization to a computing system for display by the computing system, wherein the computing system comprises an augmented reality (AR) system or a virtual reality (VR) system.

13. The system of claim 12, wherein the one or more processors are further to implement a processing pipeline that is customized by:

receiving a selection of at least the one or more selected neural networks from a pool of neural networks for processing data; and configuring the processing pipeline to include at least one of the one or more selected neural networks and at least one of the one or more selected neural network data processing programs.

14. The system of claim 13, wherein the one or more selected neural network data processing programs includes a pre-processing operation for preparing the data for the one or more selected neural networks.

15. The system of claim 13, wherein the one or more processors are further to:

receive a request from a computing device to perform one or more operations on the data; and use the processing pipeline to apply at least one of the one or more selected neural network data processing programs to perform the one or more operations on the data in the request.

16. The system of claim 12, wherein the one or more selected neural networks includes at least one of: a computer vision algorithm, an object detection algorithm, an image reconstruction algorithm, and a gene sequencing algorithm.

17. The system of claim 16, wherein the one or more selected neural networks is used to perform one or more tasks including an object detection task, a feature detection task, a segmentation task, a reconstruction task, a calibration task, or an image enhancement task.

18. The system of claim 12, wherein the one or more processors are further to use a visualization service to display the data generated from the inferencing by the one or more selected neural networks.

19. One or more processors, comprising:

circuitry to implement a sequence of processing operations using information generated by one or more selected neural networks performing one or more selected neural network data processing programs, and to execute a web-based service, the web-based service comprising:

a user interface to allow one or more users of the web-based service to select the one or more selected neural network data processing programs from a container registry and the one or more selected neural networks from a model registry, wherein the model registry comprises a plurality of neural networks trained on data in different locations to perform different inferencing tasks and wherein the sequence of processing operations include a combination of:

inferencing using the one or more selected neural networks, generating a visualization based, at least in part, on data generated from the inferencing by the one or more selected neural networks, and transmitting display data corresponding to the visualization to a computing system for display by the computing system, wherein the computing system comprises an augmented reality (AR) system or a virtual reality (VR) system.

20. The one or more processors of claim 19, wherein the circuitry is further to enable the one or more users to implement a pipeline by selecting the one or more selected neural networks from the model registry and selecting the one or more selected neural network data processing programs from the container registry.

21. The one or more processors of claim 20, wherein the model registry includes one or more machine learning models trained to perform at least one processing task with respect to digital imaging and communications in medicine (DICOM) data, radiology information system (RIS) data, clinical information system (CIS) data, remote procedure call (RPC) data, data substantially compliant with a representation state transfer (REST) interface, data substantially compliant with a file-based interface, or raw data.

22. The one or more processors of claim 19, wherein the circuitry is further to:

receive a request to perform one or more operations on data;

identify a format of the data before data is used to train the one or more selected neural networks; and use at least one of the one or more selected neural network data processing programs to perform the one or more operations on the data, based on the identified format, before data is used to train the one or more selected neural networks.

23. The one or more processors of claim 22, wherein the one or more operations on the data comprise converting the data to another format suitable for processing by the one or more selected neural networks.

24. The one or more processors of claim 19, wherein the circuitry is further to:

identify a format of the data generated by the one or more selected neural networks; and use at least one of the one or more selected neural network data processing programs to process the data generated by the one or more selected neural networks, based on the identified format, before transmitting the data to a display device.

* * * * *